United States Patent [19]

Palmer

[11] Patent Number: 5,686,610

[45] Date of Patent: Nov. 11, 1997

[54] PYRIDYL PIPERAZINE COMPOUND

[75] Inventor: John R. Palmer, Kalamazoo, Mich.

[73] Assignee: Pharmacia & Upjohn Company, Kalamazoo, Mich.

[21] Appl. No.: 711,822

[22] Filed: Sep. 10, 1996

Related U.S. Application Data

[63] Continuation of Ser. No. 197,589, Feb. 17, 1994, Pat. No. 5,599,930, which is a continuation of Ser. No. 176,030, filed as PCT/US92/05067 Jun. 23, 1992, abandoned, which is a continuation-in-part of Ser. No. 725,053, Jul. 3, 1991, abandoned.

[51] Int. Cl.$^6$ .................................................. C07D 401/04
[52] U.S. Cl. ................................................................ 544/360
[58] Field of Search .................................................. 544/360

[56] References Cited

U.S. PATENT DOCUMENTS

| | | |
|---|---|---|
| 3,146,234 | 8/1964 | Archer . |
| 3,472,855 | 10/1969 | Archer . |
| 5,032,598 | 7/1991 | Baldwin et al. . |
| 5,120,843 | 6/1992 | McCall et al. . |
| 5,175,281 | 12/1992 | McCall et al. . |
| 5,215,989 | 6/1993 | Baldwin et al. . |
| 5,489,593 | 2/1996 | Palmer et al. ............... 544/360 |

FOREIGN PATENT DOCUMENTS

| | | |
|---|---|---|
| 370381A2 | 5/1990 | European Pat. Off. . |
| 9109849 | 7/1991 | European Pat. Off. . |
| 01132579 | of 1987 | Japan . |

OTHER PUBLICATIONS

Drug News & Perspective, 5(3), 153–169 (1992).
Aids Research and Human Retroviruses, 8(6), 963–990 (1992).
Viniti, 3979–82 (1982).
Chem. Abst. 100(7) 51549b (1984).
Indian J. Chem. Sect. B, 17B(3), 246–9 (1979).
Indian J. Med. Res., 63(10), 1418–25 (1975).
Proceedings of the National Academy of Science, 88, 8806–10 (1991).

*Primary Examiner*—Robert W. Ramsuer
*Attorney, Agent, or Firm*—Bruce Stein

[57] ABSTRACT

Substituted indoles of formula (I)

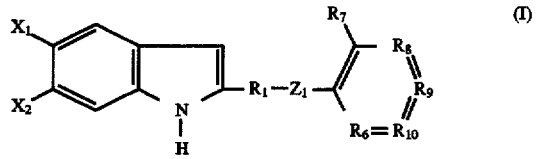

are useful anti-AIDS pharmaceuticals.

1 Claim, No Drawings

PYRIDYL PIPERAZINE COMPOUND

CROSS REFERENCE TO RELATED APPLICATIONS

The present patent application is a continuation of patent application Ser. No. 08/197,589, filed Feb. 17, 1994, now U.S. Pat. No. 5,599,930, which is a continuation of U.S. patent application Ser. No. 08/176,030, filed Dec. 30, 1993 now abandoned which was a continuation (national phase) application of PCT/US92/05067, filed Jun. 23, 1992 which was a continuation-in-part application of U.S. patent application Ser. No. 07/725,053, filed Jul. 3, 1991, now abandoned.

BACKGROUND OF THE INVENTION

1. Field of the Invention

The oxygen and nitrogen substituted indoles described are useful in the treatment of AIDS.

2. Description of the Related Art

International Publication No. WO 87/01797 (U.S. Pat. No. 5,175,281) discloses compounds which can be visualized as steroid-piperazine-[substituted aromatic] or steroid-piperazine-[substituted heteroaromatic]. The steroid and piperazine being "connected" via the $C_{17}$ side-chain of the steroid.

International Publication No. WO 88/08424 (U.S. Pat. No. 5,120,843) disclosed compounds which can be visualized as aromatic-connector-piperazine-[substituted aromatic] or aromatic-connector-piperazine-[substituted heteroaromatic], in particular see the compounds of formulas (I) and (III). None of those compounds were disclosed as having the utility set forth in this invention. In U.S. Pat. No. 5,120,843 it was disclosed that the compounds of formula (I) of International Publication No. WO 88/08424 were useful against AIDS.

An estimated one to one and one-half million people in the United States are infected with a human retrovirus, the human immunodeficiency virus type I (HIV-1) which is the etiological agent of acquired immunodeficiency syndrome, AIDS, see Science, 661–662 (1986). Of those infected, an estimated two hundred and fifty thousands people will develop AIDS in the next five years, see Science, 1352–1357 (1985). On Mar. 20, 1987, the FDA approved the use of the compound, AZT (zidovudine), to treat AIDS patients with a recent initial episode of pneumocystis carinii pneumonia, AIDS patients with conditions other than pneumocystis carinii pneumonia or patients infected with the virus with an absolute CD4 lymphocyte count of less than 200/mm³ in the peripheral blood. AZT is a known inhibitor of viral reverse transcriptase, an enzyme necessary for human immunodeficiency virus replication.

U.S. Pat. No. 4,724,232 claims a method of treating humans having acquired immunodeficiency syndrome utilizing 3'-azido-3'-deoxy-thymidine (azidothymidine, AZT).

Following the discovery of the anti-HIV activity of AZT, much effort has been focused on a wide variety of other dideoxynucleoside analogues in the search for superior agents. In the case of the 2',3'-dideoxy series, ddC and ddI have shown potent activity against HIV in vitro and have been evaluated in clinical trials, see *Drug News & Perspectives*, 5(3) 153–169 (1992) in particular page 160. The FDA has approved ddI for the treatment of HIV-1 infections in adults and pediatrics patients who are intolerant to, or whose health has significantly deteriorated while on, AZT treatment, see *AIDS Research and Human Retroviruses*, 8(6), 963–990, 1992 (1992) in particular page 966.

It is known in the art that certain antibiotics and polyanionic dyes inhibit retrovirus reverse transcriptase.

Many publications have reported the ability of various sulfated compounds to inhibit virus replication, including HIV.

Nature 343, 470 (1990) and Science 250, 1411 (1990) discloses potent benzodiazepin type reverse transcriptase inhibitors. The compounds of the present invention are not benzodiazepin type compounds.

U.S. Pat. Nos. 3,146,234 and 3,188,313 discloses compounds of the general formula

[substituted indol-2-yl]-$(CH_2)_n$-[piperazinyl type]-[pyridinyl/pyrimidinyl].

The substituted indoles (I) of the present invention differ from the prior art compounds in that the substitution on the $-\phi$ ring of the indole is a different group than that of the group in U.S. Pat. No. 3,188,313.

VINITI, 3979–82 (1982) in Russian and *Chem. Abst.* 100(7) 51549b (1984) discloses a compound which can be represented as 5-methoxy[indol-2-yl]-CO-piperazinyl-[2-quinolinyl]

which differs from the claimed compounds in that none of the claimed compounds have quinoline structure or any bicyclic structure attached to the piperazinyl moiety.

JP 01132579 (1987) discloses compounds which can be represented as (optionally substituted)-[indol-2-yl]-CO-piperazinyl-$(CH_2)_n$-[pyridinyl]

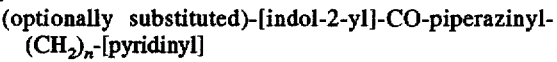

which have very strong blood platelet agglutination inhibiting activity where n is 1–5 which differs from the claimed compounds in that the claimed compounds do not permit any linking group between the piperazinyl moiety and the phenyl or pyridinyl substituent.

*Indian J. Chem. Sect. B*, 17B(3), 246–9 (1979) and *Indian J. Med. Res.*, 63(10), 1418–25 (1975) disclose compounds which can be represented as (non-substituted)-[indol-2-yl]-CO-piperazinyl-$(CH_2)_n$-[optionally substituted) phenyl]

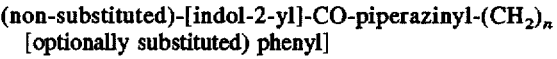

The *Indian J. Chem. Sect. B*, 17B(3), 246–9 (1979) reported on p. 247 that none of the compounds showed any noteworthy (CNS) biological activity. The *Indian J. Med. Res.*, 63(10), 1418–25 (1975) reported some of the compounds they prepared had anti-vital activity against Semliki forest virus (SFV) in mice. One compound, a dihydroisoquinolin was tested and found to be inactive against new castle disease virus in chick embryo. These compounds differ from the claimed compounds in that the claimed compounds require the indole group to be substituted.

International Publication EP 370 381 A2, published 5 May 90 discloses compounds which can be represented as

[heteroaryl]-CO-piperazinyl-[quinolinone]

where heteroaryl includes 2-indolyl which differ from the claimed compounds in that none of the claimed compounds have quinoline structure or any bicyclic structure attached to the piperazinyl moiety. The disclosed compounds possess cardiotonic and hypotensive activities and the capability of reducing the heart rate.

U.S. Pat. Nos. 5,032,598 and 5,215,989 discloses class III anti-arrhythmic compounds of the formula $R^2R^3Ar$—[B]—X—Q—Y—$R^1$

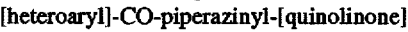

which if the appropriate substituents were selected generically encompasses some of the compounds of the present invention.

U.S. Pat. Nos. 3,472,855 and 3,562,278 disclose 3-indolinyl compounds which are useful as psychomotor depressants. The substituted indoles (I) of the present inven-

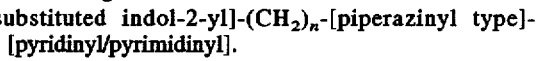

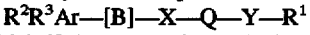

tion are useful for a totally different purpose, inhibition of HIV-RT and treatment of AIDS.

U.S. Pat. No. 3,362,956 discloses compounds of the general formula

[3-quinolyl]-$(CH_2)_n$-[piperazinyl type]-[pyridinyl/phenyl].

The substituted indoles (I) of the present invention differ from the prior art compounds in that they do not include 3-quinolyl type compounds.

U.S. Pat. No. 3,472,854 discloses compounds of the general formula

[2-benzimidazolyl]-$(CH_2)_n$-[piperazinyl type]-[pyridinyl/phenyl].

The substituted indoles (I) of the present invention differ from the prior art compounds in that they are indoles and not 2-benzimidazolyl type compounds.

U.S. Pat. No. 3,491,098 discloses compounds of the general formula

[4(5)-imidazolyl]-$(CH_2)_n$-[piperazinyl type]-[pyridinyl/phenyl].

The substituted indoles (I) of the present invention differ from the prior art compounds in that they are indoles and not imidazolyl type compounds.

U.S. Pat. No. 3,511,841 discloses compounds of the general formula

[azaindolyl]-$(CH_2)_n$-[piperazinyl type]-[pyridinyl/phenyl]

[azaindolyl]-CO-[piperazinyl type]-[pyridinyl/phenyl]

The substituted indoles (I) of the present invention differ from the prior art compounds in that they are they have substituted oxygen or substituted amino groups on the —φ portion of the indole and do not contain nitrogen in the ring.

U.S. Pat. No. 4,302,589 discloses 3-indolinyl compounds with a methyl group at the $C_2$ position of the indole and an ethyl bridge between the indole and piperazine which are useful as anti-psychotics. The substituted indoles (I) of the present invention are useful for a totally different purpose, inhibition of HIV-RT and treatment of AIDS.

European patent publication 345,808 discloses 3-indolinyl-piperazinyl-[substituted 2-pyridinyl] compounds (example 66) which are useful as anti-depressants. The substituted indoles (I) of the present invention are useful for a totally different purpose, inhibition of HIV-RT and treatment of AIDS.

International Publication No. WO 91/09849 (published Jul. 11, 1991) discloses diaromatic substituted heterocyclic compounds of the type [ARYL/HETEROARYL]-CONNECTOR-PIPERAZINE TYPE-ARYL/HETEROARYL useful in treating individuals infected with the HIV virus.

*Proceedings of the National Academy of Sciences* 88, 8806–10 (1991) discloses various bis(heteroaryl)piperazinyl non-nucleoside reverse transcriptase inhibitors which potently and specifically block human immunodeficiency virus type 1 replication.

There are a number of other chemically unrelated compounds which have been reported to inhibit HIV and/or be useful in the treatment of AIDS.

SUMMARY OF INVENTION

Disclosed are substituted indoles of formula (I)

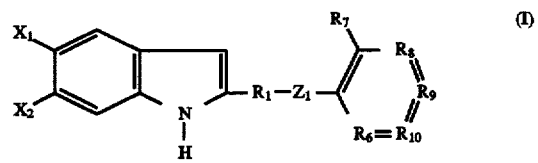

where $R_1$ is —$CH_2$— or —CO—;
where $Z_1$ is

where $n_1$ is 1 or 2 and $n_2$ is 1 or 2,

where $Z_2$ is —$N(Z_{2-1})$— where $Z_{2-1}$ is $C_1$-$C_4$ alkyl and where $n_1$ and $n_2$ are as defined above;
where $X_1$ and $X_2$ are
—H,
—O—$C_1$-$C_3$ alkyl,
—O—$(CH_2CH_2$—O—$)_{n3}$—$X_{1-1}$ where $n_3$ is 1 thru 4, where $X_{1-1}$ is —H or $C_1$-$C_4$ alkyl,
—O—$SO_2$—$(CH_2)_{n4}$—$N(X_{1-2})(X_{1-3})$ where $n_4$ is 1 thru 3, where $X_{1-2}$ and $X_{1-3}$ are the same or different and are —H, $C_1$-$C_6$ alkyl, —φ, 2-pyridinyl, 3-pyridinyl, 4-pyridinyl and where $X_{1-2}$ and $X_{1-3}$ can be taken together with the attached nitrogen atom, and other heteroatom if necessary, to form a ring selected from the group consisting of 1-pyrrolidinyl, 1-piperidinyl, 1-piperazinyl, 1-morpholinyl and 1-piperazinyl optionally substituted
 in the 4-position with $C_1$-$C_5$ alkyl,
 in the 3- and/or 5- position with $C_1$-$C_3$ alkyl, and N-oxides thereof
—O—$SO_2$—$(CH_2)_{n4}$—$X_{1-8}$ where $X_{1-8}$ is 2-pyridinyl, 3-pyridinyl and 4-pyridinyl and where $n_4$ is as defined above,
—O—CO—$(CH_2)_{n4}$—$NX_{1-2}X_{1-3}$ where $n_4$, $X_{1-2}$ and $X_{1-3}$ are as defined above,
—NH—CO—$(CH_2)_{n4}$—$NX_{1-2}X_{1-3}$ where $n_4$, $X_{1-2}$ and $X_{1-3}$ are as defined above,
—$N(X_{1-4})$—$SO_2X_{1-5}$ where $X_{1-4}$ is $C_1$-$C_3$ alkyl, where $X_{1-5}$ is $C_1$-$C_4$ alkyl and where $X_{1-4}$ and $X_{1-5}$ are taken together to form a heterocyclic ring of 5 or 6 atoms,
—$N(X_{1-7})$—CO—$N(X_{1-7})$—$(CH_2)_{n4}$—$N(X_{1-2})(X_{1-3})$ where the $X_{1-7}$s are the same different and are —H or $C_1$-$C_3$ alkyl, and where $n_4$, $X_{1-2}$ and $X_{1-3}$ are as defined above,
—$N(X_{1-7})$—$SO_2$—$(CH_2)_{n4}X_{1-8}$ where $n_4$, $X_{1-7}$ and $X_{1-8}$ are as defined above,
—$N(X_{1-7})$—CO—$N(X_{1-7})$—$(CH_2)_{n5}$—$X_{1-8}$ where $n_5$ is 0 thru 3 and where $X_{1-7}$ and $X_{1-8}$ are as defined above,
—$N(X_{1-7})$—$SO_2$—$(CH_2)_{n4}$—$N(X_{1-2})(X_{1-3})$ where $n_4$, $X_{1-2}$, $X_{1-3}$ and $X_{1-7}$ are defined above,
—$N(X_{1-7})$—CO—O—$X_{1-6}$ where $X_{1-6}$ is $C_1$-$C_4$ alkyl or —$(CH_2)_{n4}$—$N(X_{1-2})(X_{1-3})$ where $n_4$, $X_{1-2}$, $X_{1-3}$ and $X_{1-7}$ are as defined above, —N($X_{1-7}$)—CO—N($X_{1-2}$)($X_{1-3}$) where $X_{1-2}$, $X_{1-3}$ and $X_{1-7}$ are as defined above, NH—CO—CF$_3$,
—O—SO$_2$—CF$_3$,
—NH—SO$_2$—CF$_3$,
—N($X_{1-7}$)—SO$_2$—N($X_{1-2}$)($X_{1-3}$) where $X_{1-2}$, $X_{1-3}$ and $X_{1-7}$ are as defined above,
—NH—CO—[4-(1-$X_{1-2}$)piperidinyl], with the proviso that one, but only one, of $X_1$ or $X_2$ must be —H or —O—$C_1$-$C_3$ alkyl, $R_6$ is —N=,
—CH=,
—N(O)=, $R_7$ is —COO—$R_{7-11}$ where $R_{7-11}$ is
$C_1$-$C_6$ alkyl,
—CO—N($R_{7-3}$)($R_{7-4}$) where $R_{7-3}$ and $R_{7-4}$ are the same or different and are —H or $C_1$-$C_6$ alkyl,
—N($R_{7-5}$)($R_{7-6}$) where $R_{7-5}$ is
$C_1$-$C_6$ alkyl,
—C($R_{7-15}$)($R_{7-16}$)—($R_{7-17}$) where $R_{7-15}$ and $R_{7-16}$ are the same or different and are —H or $C_1$-$C_3$ alkyl and where $R_{7-17}$ is $C_2$-$C_5$ alkenyl containing 1 or 2 double bonds or $C_2$-$C_5$ alkynyl containing 1 triple bond,
—CH$_2$—CH$_2$—OH,
—CH$_2$—CH$_2$—CH$_2$—OH,
—CH(CH$_3$)CH$_2$—O—CH$_3$,
—CH(CH$_3$)CH$_2$—OH,
—CH$_2$—CF$_3$,
—CH$_2$-cyclopropyl,
—CH$_2$—CH$_2$F,
—CH$_2$—CH$_2$—C≡N,
—C*$R_{7-18}$—(CH$_2$)$_{n14}$—C*H$_2$ where $R_{7-18}$ is —H or —CH$_3$, $n_{14}$ is 1 thru 5 and the carbon atoms marked with an asterisk (*) are bonded to each other to resulting in the formation of a ring,
—(CH$_2$)$n_1$—N($R_{7-7}$)($R_{7-8}$) where $n_1$ is as defined above and where $R_{7-7}$ and $R_{7-8}$ are the same or different and are —H or $C_1$-$C_4$ alkyl, and where $R_{7-7}$ and $R_{7-8}$ are taken together with the attached nitrogen atom to form a heterocyclic ring selected from the group consisting of 1-pyrrolidinyl, 1-piperidinyl, 1-piperazinyl or N-morpholinyl, 1-aziridinyl, and where $R_{7-6}$ is —H,
$C_1$-$C_6$ alkyl,
—C($R_{7-15}$)($R_{7-16}$)—($R_{7-17}$) where $R_{7-15}$, $R_{7-16}$ and $R_{7-17}$ are as defined above,
—CH$_2$—CH$_2$—OH,
—CH$_2$—CH$_2$—CH$_2$—OH,
—CH$_2$CF$_3$,
—CH$_2$—CH$_2$F,
—CH$_2$—CH$_2$—C≡N,
or where $R_{7-5}$ and $R_{7-6}$ are taken together with the attached nitrogen atom to form a heterocyclic ring selected from the group consisting of 1-pyrrolidinyl, 1-piperidinyl, 1-piperazinyl, N-morpholinyl or 1-aziridinyl,
—(CH$_2$)$_{n4}$—N($R_{7-9}$)($R_{7-10}$) where $n_4$ is as defined above and where $R_{7-9}$ and $R_{7-10}$ ar the same or different and are —H or $C_1$-$C_4$ alkyl, and where $R_{7-9}$ and $R_{7-10}$ are taken together with the attached nitrogen atom to form a heterocyclic ring selected from the group consisting of 1-pyrrolidinyl, 1-piperidinyl, 1-piperazinyl or N-morpholinyl, $R_8$ is —N=,
—CR$_{8-1}$= where $R_{8-1}$ is —H, —F, —Cl, —Br, —CF$_3$,
—NO$_2$, —COCF$_3$,
$C_1$-$C_6$ alkyl,
$C_1$-$C_3$ alkylthio,
—OH,
—O—$R_{8-2}$ where $R_{8-2}$ is $C_1$-$C_6$ alkyl, –φ, —CO—$R_{8-3}$ where $R_{8-3}$ is $C_1$-$C_6$ alkyl or –φ,
—NH($R_{8-4}$) where $R_{8-4}$ is
$C_1$-$C_6$ alkyl,
—C($R_{8-7}$)($R_{8-8}$)—($R_{8-9}$) where $R_{8-7}$ and $R_{8-8}$ are the same or different and are —H or $C_{C3}$ alkyl and where $R_{8-9}$ is $C_2$-$C_5$ alkenyl containing 1 or 2 double bonds or $C_2$-$C_5$ alkynyl containing 1 triple bond,
—NR$_{8-5}$—CO—$R_{8-6}$ where $R_{8-5}$ is —H or $C_1$-$C_6$ alkyl and $R_{8-6}$ is —H, $C_{1-C6}$ alkyl or $C_1$-$C_3$ alkoxy;

$R_9$ is —N=,
—CR$_{9-1}$= where $R_{9-1}$ is —H, —F, —Cl, —Br,
—NO$_2$, —COCF$_3$,
$C_1$-$C_6$ alkyl,
$C_1$-$C_3$ alkylthio,
—OH,
—O—$R_{9-2}$ where $R_{9-2}$ is $C_1$-$C_6$ alkyl, –φ, —CO—$R_{9-3}$ where $R_{9-3}$ is $C_1$-$C_6$ alkyl or –φ,
—N($R_{9-4}$)($R_{9-5}$) where $R_{9-4}$ and $R_{9-5}$ are the same or different and are
—H,
$C_1$-$C_6$ alkyl,
—C($R_{9-8}$)($R_{9-9}$)—($R_{9-10}$) where $R_{9-8}$ and $R_{9-9}$ are the same or different and are —H or $C_1$-$C_3$ alkyl and where $R_{9-10}$ is $C_2$-$C_5$ alkenyl containing 1 or 2 double bonds or $C_2$-$C_5$ alkynyl containing 1 triple bond,
$R_{9-4}$ and $R_{9-5}$ are taken together with the attached nitrogen atom to form a heterocyclic ring selected from the group consisting of 1-pyrrolidinyl, 1-piperidinyl, 1-piperazinyl or N-morpholinyl,
—NR$_{9-6}$—CO—$R_{9-7}$ where $R_{9-6}$ is —H or $C_1$-$C_6$ alkyl and $R_{9-7}$ is —H, $C_1$-$C_6$ alkyl or $C_1$-$C_3$ alkoxy;

$R_{10}$ is —N=,
—CR$_{10-1}$= where $R_{10-1}$ is —H, —F, —Cl, —Br, —CF$_3$,
—NO$_2$, —COCF$_3$,
$C_1$-$C_6$ alkyl,
$C_1$-$C_3$ alkylthio,
—OH,
—O—$R_{10-2}$ where $R_{10-2}$ is $C_1$-$C_6$ alkyl, –φ, —CO—$R_{10-3}$ where $R_{10-3}$ is $C_1$-$C_6$ alkyl or –φ,
—N($R_{10-4}$)($R_{10-5}$) where $R_{10-4}$ and $R_{10-5}$ are the same or different and are
—H,
$C_1$-$C_6$ alkyl,
—C($R_{10-8}$)($R_{10-9}$)—($R_{10-10}$) where $R_{10-8}$ and $R_{10-9}$ are the same or different and are —H or $C_1$-$C_3$ alkyl and where $R_{10-10}$ is $C_2$-$C_5$ alkenyl containing 1 or 2 double bonds or $C_2$-$C_5$ alkynyl containing 1 triple bond, —NR$_{10-6}$—CO—$R_{10-7}$ where $R_{10-6}$ is —H or $C_1$-$C_6$ alkyl and $R_{10-7}$ is —H, $C_1$-$C_6$ alkyl or $C_1$-$C_3$ alkoxy; with the proviso that not more than two of $R_6$, $R_8$, $R_9$ and $R_{10}$ are —N=; enantiomers, pharmaceutically acceptable salts, hydrates and solvates thereof.

Also disclosed are compounds selected from the group consisting of

1-[5-(piperadin-4-yl)amido)indolyl-2-carbonyl]-4-[3-(1-methylethylamino)-2-pyridinyl]piperazine, 1-[5-((1-(1-methylethylpiperadin-4-yl)amido)indolyl-2-carbonyl]-4-[3-(1-methylethylamino)-2-pyridinyl]piperazine, 1-[5-methoxycarbamoylindolyl-2-carbonyl]-4-[3-(1-methylethylamino)-2-pyridyl]-piperazine, 1-[5-(1',1'-dioxo-2'-isothiazolidinyl)indolyl-2-carbonyl]-4-[3-(1-methylethylamino)-2-pyridyl]piperazine, 1-[5-(trifluoromethanesulfonamido)indolyl-2-carbonyl]-4-[3-(1-methylethylamino)-2-pyridyl]piperazine and pharmaceutically acceptable salts thereof.

Further disclosed are compounds selected from the group consisting of

1-[5-aminoindole-2-carbonyl]-4-[3-(1,1-dimethylpropylamino)-2-pyridinyl]piperazine, 1-[5-(methanesulfonamido)indole-2-carbonyl]-4-[3-(1,1-dimethylpropylamino)-2-pyridinyl]piperazine, 1-[5-methanesulfonamidoindole-2-carbonyl]-4[N-methyl-N-(3-(1,1-dimethylpropylamino)-2-pyridinyl)amino]piperidine, 1-[6-(2-(1-piperadinyl)ethoxy)indolyl-2-carbonyl]-4-[3-(1-methylethyl-amino)-2-pyridinyl]piperazine, 1-[5-methoxy-6-(2-(1-morpholinyl)ethoxy)indolyl-2-carbonyl]-4-[3-(1-methylethylamino)-2-pyridinyl]piperazine and pharmaceutically acceptable salts thereof.

DETAILED DESCRIPTION OF THE INVENTION

The substituted indoles (I) of the present invention are prepared by known methods from known starting materials. The invention is the substituted indoles (I), not the methods to prepare them.

For the substituted indoles (I), it is required with regard to $X_1$ or $X_2$ that one, but only one, of $X_1$ or $X_2$ must be —H or —O—$C_1$-$C_3$ alkyl.

Depending on whether the heteroatom attaching the X group to the indole is oxygen (—O—) or nitrogen (—NH—) the substituted indoles (I) are made by different procedures.

When the heteroatom is an oxygen atom, the substituted indoles (I) are prepared as set forth in CHART A. CHART A exemplifies production of the substituted indole (I) with an oxygen atom at the 6-position of the indole nitrogen, at $X_2$. However, it should be realized the synthetic process set forth in CHART A is equally applicable when the oxygen function is at the 5-position of the indole, at $X_1$. The synthetic process begins with the appropriate hydroxyaldehyde (II). The hydroxyaldehyde (II) then has the remaining portion of the desired X group added, by known means, to form X—O—, to produce the substituted aldehyde (III). The substituted aldehyde (III) is then reacted with α-azidomethylester, preferably the acetate to form the corresponding azide (IV). The reaction is performed in a polar solvent, preferably an alcohol such as methanol and cooled to about −10°. A base such as sodium methoxide in methanol is added dropwise. The reaction is warmed to 20°–25° until TLC indicates the reaction is complete. The azide (IV) is transformed to the corresponding indole ester (V) by heating to reflux in a solvent such as xylene. The indole ester (V) is then hydrolyzed to the corresponding indole acid (VI). The indole acid (VI) is the coupled with the desired amine substituent ($Z_1$-aromatic portion) to form the substituted indole (I), see EXAMPLE 5. The desired amine substituent ($Z_1$-aromatic portion) are either known to those skilled in the art (in particular see International Publication No. WO 87/01797, PREPARATION A-1 thru PREPARATION A-50) or can readily be prepared be prepared from known compounds by methods well known to those skilled in the art. The reaction of the indole acid (VI) and the desired amine substituent ($Z_1$-aromatic portion) is a very well known reaction. When $Z_1$ is the molecular fragment (Z-I) which is a piperazine, the amine substituent is a secondary amine and the reaction with the appropriate indole acid (VI) produces an amide. Should the indole acid be reduced to an indole alcohol ($R_1$ is —$CH_2$—), alkyl halide formed then the substituted indole (I) will be a tertiary amine. The reaction to produce tertiary amines or amides from cyclic amines such as piperazine is very well known to those skilled in the art and requires no special mention. See International Publication Nos. WO 87/01797 and WO 88/08424.

When the heteroatom attaching the X group to the indole is a nitrogen, the substituted indoles are made by the process of CHART B. The amino indoles (VII) are known to those skilled in the art or can be readily be prepared by known means from known starting materials. The amino indoles (VII) are reacted with the sulfonyl chloride, Cl—($CH_2$)$_2$—$SO_2$—Cl (VIII) to produce the corresponding ethylene sulfonamide (IX). The ethylene sulfonamide (IX) is then reacted with the desired amine and powdered copper catalyst under reflux to produce the desired substituted indole (I). Similarly amino indoles (VII) can be reacted with Cl—($CH_2$)$_3$—$SO_2$—Cl to produce the 3-chloropropylsulfonamides. Alkylation with an amine would produce the desired substituted indoles. Alternatively, one can react the amino or hydroxy indole with functionalized sulfonyl chlorides, which are known in the art, such as 2-(4-pyridyl)ethane sulfonyl chloride to provide the sulfonamides or sulfonates directly.

The process used for synthesizing the substituted indoles (I) where the atom attaching the X group to the indole is nitrogen does not work well when the atom is oxygen because if one starts with the hydroxy indole corresponding to the amino indole (VII), and attempts to alkylate as is done in the synthesis of compound (III), CHART A, then nitrogen atom of the indole would be competitively alkylated. This is not a problem with sulfonylation of the amino indole (VII) because the amino group on the benzene reacts preferentially over the indole nitrogen with R—$SO_2$-leaving group.

The amino indole (VII) can be transformed into the desired indole (I) where $X_1$ or $X_2$ is a urea ($R_aR_b$—N—CO—NH—indole-) by reacting the free amino group on the indole with an isocyanate, by known means, see EXAMPLES 18–20. Another way to produce the substituted indole (I) where $X_1$ or $X_2$ is a urea is by reaction of the free amino group in the indole with phosgene (or a phosgene equivalent such as carbonyldiimidazole) and trapping with an amine. As is apparent to those skilled in the art, isothiocyanates or thiophosgene equivalents could be used to produce the corresponding —CS— compounds. Likewise, reaction of the amino indole (VII) with X—$SO_2$—X followed by reaction with an amine produces sulfamides, $R_aR_bN$—$SO_2$—NH-indole by means known to those skilled in the art.

The substituted indoles (I) where $R_1$ is —$CH_2$— can be produced from the corresponding substituted indoles (I) where $R_1$ is —CO— by reaction with a reducing agent, such as lithium aluminum hydride in an ether such as tetrahydrofuran or ether. Alternatively, one can use starting materials in which $R_1$ is methylene rather than a carbonyl group.

It is preferred that $Z_1$ is (Z-I) where $n_1$ and $n_2$ are 1. It is also preferred that $Z_1$ is (Z-II where $n_1$ and $n_2$ are 1. When $Z_1$ is Z-II it is preferred that $Z_{2-1}$ is $C_1$ alkyl.

It is preferred that $R_1$ is —CO—.

It is preferred that $R_6$ is —N=.

It is preferred that for $R_8$, $R_9$ and $R_{10}$ are $R_8$ is —$CR_{8-1}$= where $R_{8-1}$ is —H, where $R_9$ is —$CR_{9-1}$= where $R_{9-1}$ is —H and where $R_{10}$ is —$CR_{10-1}$= where $R_{10-1}$ is —H.

It is preferred that $R_7$ is $-N(R_{7-5})(R_{7-6})$ where $R_{7-5}$ is $C_2$–$C_4$ alkyl and where $R_{7-6}$ is —H. It is preferred that $R_{7-5}$ is i-propyl.

It is preferred that one of $X_1$ or $X_2$ is selected from the group consisting of $-N(X_{1-7})-CO-N(X_{1-2})(X_{1-3})$ and
$-N(X_{1-7})-SO_2-N(X_{1-2})(X_{1-3})$.

It is preferred that the other of $X_1$ or $X_2$ is —H or alkoxy.

It is preferred that the substituted indole (I) is selected from the group consisting of compounds of EXAMPLES 5, 9, 14–20, 28–30, 32, 34–37, 39, 40, 42, 44, 46–56, 58–61, 63–65, 69–73, 75 and 76. It is more preferred that the substituted indole (I) is selected from the group consisting of compounds of EXAMPLES 35, 37, 42, 55 and 57; it is even more preferred that the substituted indole (I) is selected from the group consisting of compounds of EXAMPLES 35, 37 and 57. The compounds of EXAMPLES 33, 38, 67, 68 and 74 are not within the scope of claim 1 and therefore are claimed in a claim not dependent on claim 1. In addition, intermediates of EXAMPLES 1–4, 8, 10–13, 21, 31 are claimed.

The substituted indoles (I) are amines, and as such form acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids methanesulfonic, hydrochloric, hydrobromic, sulfuric, phosphoric, nitric, benzoic, citric, tartaric, fumaric, maleic, $CH_3-(CH_2)_n-COOH$ where n is 0 thru 4, $HOOC-(CH_2)n-COOH$ where n is as defined above.

The substituted indoles (I) are useful as inhibitors of viral reverse transcriptase, an enzyme necessary for human immunodeficiency virus replication and therefore would be useful in the treatment of such diseases as AIDS.

The term human retrovirus (HRV) indicates human immunodeficiency virus type I, or strains thereof apparent to one skilled in the art, which belong to the same viral families and which create similar physiological effects in humans as various human retroviruses.

Patients to be treated would include those individuals (1) infected with one or more than one strain of a human retrovirus as determined by the presence of either measurable viral antibody or antigen in the serum and (2) having either a symptomatic AIDS defining infection such as (a) disseminated histoplasmosis, (b) isopsoriasis, (c) bronchial and pulmonary candidiasis including pneumocystic pneumonia (d) non-Hodgkin's lymphoma or (e) Kaposi's sarcoma and being less than sixty years old; or having an absolute CD4 lymphocyte count of less than 200/m³ in the peripheral blood.

The substituted indoles (I) can be given orally. Suitable dosage forms include tablets, capsules, suspensions, solutions and elixirs. An effective amount is from about 0.1 to about 500 mg/kg/day. A typical unit dose for a 70 kg human would be from about 10 mg to about 2000 mg, preferably about 100 mg to about 1000 mg taken one to six times per day.

The exact dosage and frequency of administration depends on the particular substituted indole (I) used, the particular condition being treated, the severity of the condition being treated, the age, weight, general physical condition of the particular patient, other medication the individual may be taking as is well known to those skilled in the art and can be more accurately determined by measuring the blood level or concentration of the diaromatic substituted compounds (III), the anti-AIDS piperazines (IV) and the indoles (V) in the patient's blood and/or the patient's response to the particular condition being treated.

The substituted indoles (I) of this invention can be used in conjunction with other antiviral agents such as AZT.

The utility of the substituted indoles (I) of this invention can be determined by their ability to inhibit viral reverse transcriptase, an enzyme essential for human immunodeficiency virus replication. This enzyme has characteristics which differentiate it from other known cellular polymerases and it is a unique enzyme which is not found in uninfected cells. Viral reverse transcriptase is found in extracts from bacterial clones prepared according to the procedure described in AIDS Virus Reverse Transcriptase defined by high level expression in *Escherichia coli*, EMBO J. 6:3133–3137 (1987). Inhibition of this enzyme is determined in a cell free assay which measures the level of radioactive precursors incorporated into DNA. Extracts prepared according to the procedure of *Science*, 1125–1129 (1981) are incubated in a mixture of inhibitor, 20 mM dithiothreitol, 60 mM sodium chloride, 0.05% NP-40, 10 mM magnesium chloride, 50 mM Tris pH 8.3, 10 μM [$^{35}$S]-labeled deoxynucleoside-5'-triphosphate, 10 μg/ml RNA template (poly rC or poly rG) and 5 μg/ml DNA primer (oligo dG or oligo dT) for 30 minutes at 37° C. Incorporation of radio-labeled precursor is determined by spotting aliquots of the reaction mixture on DE81 paper, washing the papers to remove unincorporated precursor, drying and determining counts. The results ($IC_{50}$ means the concentration, in μM of drug, required to inhibit the reverse transcriptase activity to the extent of 50%) of various assay(s) are combined and reported as % inhibition and $IC_{50}$ (calculated).

The utility of this invention is further demonstrated by the ability of the substituted indoles (I) to inhibit HIV-induced syncytia formation in a tissue culture assay using MT-2 cells infected with HIV-1. This test is described in Quantitative Infectivity Assay for HIV-1 and -2, *Nature* 332: 469–470, 1988 as well as in AIDS RESEARCH AND HUMAN RETROVIRUSES, Vol. 4, No. 6, pages 449–455 (1988), Mary Ann Liebent, Inc., Publishers; in an article entitled "Nucleotide Dimers Suppress HIV Expression In VITRO". The results ($IC_{50}$ means the concentration, in μM of drug, required to inhibit syncytia formation to the extent of 50%) of various assay(s) are combined and reported as % inhibition and $IC_{50}$ (calculated). The known commercial compound, AZT, exhibited anti-HIV potency in this assay with 100 percent and 50 percent reduction in syncytia formation at concentrations of approximately 1 μM and 0.5 μM, respectively.

The exact dosage and frequency of administration depends on the particular substituted indole (I) used, the particular condition being treated, the severity of the condition being treated, the age, weight, general physical condition of the particular patient, other medication the individual may be taking as is well known to those skilled in the an and can be more accurately determined by measuring the blood level or concentration of the substituted indoles (I) in the patient's blood and/or the patient's response to the particular condition being treated.

DEFINITIONS AND CONVENTIONS

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$," or "$R_i$," where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$H. Groups $R_i$ and $R_j$ would represent monovalent variable substituents if attached to the formula $CH_3$—$CH_2$—$C(R_i)$($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—$N(C_2H_5)$—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "- - -" or "...". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —$C(\alpha$-$R_{i-j})(\beta$-$R_{i-k})$—. For example, when the bivalent variable $R_6$, —$C(=R_6)$— is defined to consist of two monovalent variable substituents, the two monovalent variable substituents are $\alpha$-$R_{6-1}$:$\beta$-$R_{6-2}$, ... $\alpha$-$R_{6-9}$:$\beta$-$R_{6-10}$, etc, giving —$C(\alpha$-$R_{6-1})(\beta$-$R_{6-2})$—, ... —$C(\alpha$-$R_{6-9})(\beta$-$R_{6-10})$—, etc. Likewise for the bivalent variable $R_{11}$, —$C(=R_{11})$—, two monovalent variable substituents are $\alpha$-$R_{11-1}$:$\beta$-$R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_j$ are taken together to form —$CH_2$—$CH_2$—O—CO—..." means a lactone in which the carbonyl is bonded to $C_2$. However, when designated "... $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy ($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

THF refers to tetrahydrofuran.

DMF refers to dimethylformamide.

EDC refers to 1-ethyl-3-(dimethylaminopropyl) carbodiimide.

Saline refers to an aqueous saturated sodium chloride solution.

IR refers to infrared spectroscopy.

NMR refers to nuclear (proton) magnetic resonance spectroscopy, chemical shifts are reported in ppm ($\delta$) downfield from tetramethylsilane.

$-\phi$ refers to phenyl ($C_6H_5$).

MS refers to mass spectrometry expressed as m/e or mass/charge unit. $[M+H]^+$ refers to the positive ion of a parent plus a hydrogen atom. EI refers to electron impact. CI refers to chemical ionization. FAB refers to fast atom bombardment.

Ether refers to diethyl ether.

Alcohol refers to ethyl alcohol.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable anion salts include mesylate, chloride, sulfate, phosphate, nitrate, citrate, $CH_3-(CH_2)_{n_1}-COO^{-1}$ where $n_1$ is 0 thru 4, $^{-1}OOC-(CH_2)_{n_1}-COO^{-1}$ where n is as defined above, $^{-1}OOC-CH=CH-COO^{-1}$, $\phi-COO^{-1}$.

When solvent pairs are used, the ratios of solvents used are volume/volume (v/v).

When the solubility of a solid in a solvent is used the ratio of the solid to the solvent is weight/volume (wt/v).

Pyridinyl refers to the pyridyl radical as defined by IUPAC nomenclature. For example 2-pyridyl refers to the pyridine ring substituted in the 2-position.

The compounds of this invention are named (when possible) by the following method: first the [aryl/heteroaryl] moiety, next the aryl/heteroaryl portion and last the linker (Z). However, a few were named by other methods for simplicity and convenience. The names of the radicals within each group follow IUPAC convention.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1

1-[1,1-Dimethylethoxycarbonyl]-4-[3-(propylamino) -2-pyridinyl]piperazine

Sodium cyanoborohydride (0.31 g) is added to a cold solution of 1-[1,1-dimethylethoxycarbonyl]-4-[3-amino-2-pyridinyl]piperazine (International Publication No. WO 88/08424, 2.8 g), propional (0.87 g), and methanol (15 ml). After the exotherm has subsided, the reaction is stirred at 20°–25° overnight. The reaction is acidified (pH 2) with aqueous hydrochloride and then diluted with dichloromethane. The pH is adjusted with aqueous ammonium hydroxide (pH 8), and the phases are separated. The organic phase is dried over sodium sulfate, and concentrated under reduced pressure to a crude product which is dissolved in diethyl ether and allowed to crystallize at −5°. The solid is identified as starting material. The mother liquor is concentrated in vacuo to give the title compound.

Preparation 2

1-[3-(Propylamino)-2-pyridinyl]piperazine (Amine)

Trifluoroacetic acid (4 ml) is added to a solution of crude 1-[1,1-dimethylethoxycarbonyl]-4-[3-propylamino)-2-pyridinyl]piperazine (PREPARATION 1, 1.2 g) in dichloromethane (15 ml) chilled to −78°. The coolant is removed and the reaction is allowed to warm to 20°–25° for 3 hours. The solvents are removed in vacuo and the residue is redissolved in dichloromethane and aqueous saturated potassium carbonate. The phases are separated. The organic phase is washed with water, dried over sodium sulfate, and concentrated to the title compound.

Preparation 3

1-[1,1-Dimethylethoxycarbonyl]-4-[3-(3(1-methylethylamino)-2-pyridinyl]piperazine 1-[1,1-Dimethylethoxycarbonyl]-4-[3-amino-2-pyridinyl]piperazine (International Publication 88/08424, 2.0 g) is dissolved in 35 ml of methanol and acetone (0.48 g) is added. The reaction is cooled to 0° and acetic acid (to pH 4.0) is added. The reaction is stirred 15 min at 0° and then sodium cyanoborohydride (0.50 g) is added. The reaction is allowed to warm slowly to 20°–25° and followed by TLC until completion. Additional acetic acid, sodium cyanoborohydride and acetone are sometimes necessary to force the reaction to completion. The reaction is diluted with chloroform (100 ml), washed with saturated aqueous sodium bicarbonate (50 ml), saline (75 ml), dried over anhydrous sodium sulfate and concentrated in vacuo. Purification by flash column chromatography (75 g silica gel, 4:1 hexane/ethyl acetate) affords the title compound, NMR (300 MHz, $CDCl_3$) 7.67, 6.91, 4.15, 3.57, 3.00, 1.48 and 1.23 $\delta$.

Preparation 4

1-[3-(1-Methylethylamino)-2-pyridinyl]piperazine (Amine)

1-[1,1-Dimethylethoxycarbonyl]-4-[3-(1-methylethylamino)-2-pyridinyl]piperazine (PREPARATION 3) is dissolved in methylene chloride (56 ml) and cooled to 0°. Then trifluoroacetic acid is added dropwise. The reaction is warmed to 20°–25° and additional trifluoroacetic acid is added (26.6 g). When the reaction is complete by TLC, it is poured into 200 ml of water and ice, basified to pH 12 with 2N aqueous sodium hydroxide, and extracted with 10% tetrahydrofuran/chloroform (2 l) followed by 10% methanol/chloroform (1 l). The organic layers are dried over anhydrous sodium sulfate, concentrated in vacuo, and used without further purification, NMR (300 MHz, CDCl₃) 7.65, 6.85, 6.76, 4.16, 3.50, 2.98 and 1.20 δ.

Preparation 6

2-Chloro-3-(1-methylethylamino)pyrazine

A solution of 2,3-dichloropyrazine (2.0 g) and isopropylamine (2.3 g) in toluene (8 ml) is refluxed for 40 hr. The mixture is cooled and filtered to remove isopropylamine hydrochloride. The filtrate is concentrated in vacuo to a residue which is diluted with an aqueous sodium hydroxide solution (10%) and dichloromethane. The phases are separated. The dichloromethane phase is washed with saline, dried over sodium sulfate, and concentrated to give the title compound, NMR (CDCl₃) 1.28, 4.21, 5.02, 7.54 and 7.94 δ.

Preparation 7

1-[2-(1-Methylethylamino)-3-pyrazinyl]piperazine
(Amine)

A solution of 2-chloro-3-(1-methylethylamino)pyrazine (PREPARATION 6, 1.6 g) and piperazine (4.3 g) in xylene (10 ml) is refluxed for 26 hr. The mixture is cooled to 0° and diluted with concentrated hydrochloric acid (8 ml). The xylene is decanted and ether is added and also decanted from the salts. The salts are diluted with excess aqueous sodium hydroxide (5%) and dichloromethane. The phases are separated. The aqueous phase is extracted three more times with dichloromethane. The combined organic extracts are dried over sodium sulfate and concentrated to give a liquid mixture which is flash chromatographed on silica gel eluting with methano/chloroform (5/95). The appropriate fractions are pooled and concentrated to give the title compound, NMR (CDCl₃) 1.27, 1.83, 3.04, 4.12, 4.78, 7.49 and 7.72 δ.

Preparation 8

2-Chloro-3-(1,1-dimethylethylamino)pyrazine

Following the general procedure of PREPARATION 6 but making non-critical variations but substituting t-butyl amine of risopropylamine, the title compound is obtained, NMR (CDCl₃) 1.48, 5.24, 7.51 and 7.91 δ.

Preparation 9

1-[3-(1,1-Dimethylethylamino)-2-pyrazinyl]
piperazine (Amine)

Following the general procedure of PREPARATION 7 and making non-critical variations but starting with 2-chloro-3-(1,1-dimethylethylamino)pyrazine (PREPARATION 8, 0.95 g) and piperazine, the title compound is obtained, NMR (CDCl₃) 1.47, 1.70, 2.99, 5.02, 7.46 and 7.69 δ.

Preparation 10

1-[1,1-Dimethylethoxycarbonyl]-4-[5-amino-6-pyrimidinyl]piperazine

A mixture of 1-[1,1-dimethylethoxycarbonyl]-4-[4chloro-5-nitro-6-pyrimidyl]piperazine and triethylamine (0.3 ml) and palladium on carbon (5%, 0.13 g) in ethanol (100 ml) is charged with hydrogen gas (30 psi). After the theoretical amount of hydrogen gas is consumed, the catalyst is removed under reduced pressure. The filtrate is concentrated under reduced pressure to a foam which is diluted with an aqueous saturated solution of potassium carbonate and dichloromethane. The phases are separated and the organic phase is dried over sodium sulfate and concentrated to give to give the title compound, NMR (CDCl₃) 1.49, 3.49, 3.29, 3.56, 7.98, and 8.39 δ.

Preparation 11

1-[1,1-Dimethylethoxycarbonyl]-4-[5-(1-methylethylamino)-6-pyrimidinyl]piperazine A solution of sodium cyanoborohydride (0.13 g) in methanol (4 ml) is added to a mixture of 1-[1,1-dimethylethoxycarbonyl]-4-[5-amino-6-pyrimidinyl]piperazine (PREPARATION 10, 0.44 g), acetone (3 ml), and glacial acetic acid (0.4 ml) in methanol (7 ml) at 0°. The mixture is stirred at 20°–25° for 72 h. The reaction is diluted with an aqueous sodium hydroxide solution (10%) and dichloromethane. The phases are separated and the organic phase is washed with water and the concentrated to a colorless liquid which is flash chromatographed on silica gel eluting with methano/chloroform (1/99). The appropriate fractions are pooled and concentrated to give the title compound, NMR (CDCl₃) 1.26, 1.49, 3.2, 3.44, 3.5–3.62, 7.89 and 8.33 δ.

Preparation 12

1-[5-(1-Methylethylamino)-4-pyrimidinyl]piperazine
(Amine)

Trifluoroacetic acid (5 ml) is added to a solution of 1-[1,1-dimethylethoxy-carbonyl]-4-[5-(1-methylethylamino)-4-pyrimidinyl]piperazine (PREPARATION 11, 0.37 g) in dichloromethane (20 ml) at −78°. The reaction is allowed to warm to 20°–25° overnight, and then diluted with excess aqueous sodium hydroxide solution (10%). The phases are separated. The aqueous phase is extracted twice again with dichloromethane. The combined organic extracts are washed with saline, dried over sodium sulfate, and concentrated under reduced pressure to give the title compound, NMR (CDCl₃) 1.25, 1.7, 3.01, 3.21, 3.45, 3.5, 7.86 and 8.34 δ.

Preparation 13

1-[4-(1-Methylethyl)amino-3-pyridazinyl]piperazine
(Amine)

Following the general procedure of PREPARATION 10 and making non-critical variations but starting with 1-[5-chloro-4-(1-methylethyl)amino-3-pyridazinyl]piperazine (PREPARATION 42, 1.7 g) and triethylamine (0.81 g), the title compound is obtained, NMR (CDCl₃) 1.28, 2.06, 3.05, 3.11, 3.59, 4.75, 6.39, and 8.49 δ; CMR (CDCl₃) 22.2, 43.2, 46.2, 50.6, 103.7, 138.7, 148.4 and 154.5 δ.

Preparation 16

1-[1,1-Dimethylethoxycarbonyl]-4-[3-(1-pyrrolidinyl)-2-pyridinyl]-piperazine

1-[1,1-Dimethylethoxycarbonyl]-4-[3-amino-2-pyridinyl]piperazine (International Publication No. WO 88/08424, 0.50 g), 1,4-dibromobutane (0.21 ml) and potassium carbonate (0.30 g) are refluxed in 4 ml of acetonitrile for 1 week. After 1 week, additional dibromobutane (0.21 ml) is added and refluxing is continued for 3 days. The reaction mixture is poured into water, extracted with methylene chloride, dried over anhydrous sodium sulfate and concentrated under reduced pressure. The concentrate is purified by flash column chromatography eluting with ethyl acetate/hexane (10/90) to ethyl acetate/hexane (25/75). The appropriate fractions are pooled and concentrated to give the title compound, NMR (300 MHz, CDCl$_3$) 7.78, 6.98, 6.78, 3.52, 3.20–3.10, 1.87 and 1.44 δ.

Preparation 17

1-[3-(1-Pyrrolidinyl)-2-pyridinyl]piperazine (Amine)

1-[1,1-Dimethylethoxycarbonyl]-4-[3-(1-pyrrolidinyl)-2-pyridinyl]piperazine (PREPARATION 16, 0.26 g) is dissolved in 1.3 ml of THF and cooled to 0°. Trifluoroacetic acid (1.3 ml) is added and the reaction is stirred at 0° for 20 min, and then warmed to 20°–25° for 20 min. Then the reaction is poured into 1N aqueous sodium hydroxide and extracted with methanol/chloroform (10/90, 2×50 ml), dried over anhydrous sodium sulfate and concentrated under reduced pressure to give the title compound, NMR (300 MHz, CDCl$_3$) 7.64, 6.81, 6.61, 3.05–2.94, 2.86–2.79 and 1.78–1.65 δ.

Preparation 21

1-(3 —Nitro-2-pyridinyl)-1,4-diazepine

Homopiperazine (15.58 g) is dissolved in 100 ml of acetonitrile. Potassium carbonate (8.7 g) is added and then the 2-chloro-3-nitropyridine (5.0 g) dissolved in 25 ml of acetonitrile is added dropwise. The reaction is stirred at 20°–25° 4 hr, then diluted with methylene chloride, washed with water (2×), saline, dried over anhydrous sodium sulfate and concentrated under reduced pressure to give the title compound, NMR (300 MHz, CDCl$_3$) 8.30, 8.08, 6.66, 3.60, 3.41, 3.10, 2.89 and 1.93 δ.

Preparation 22

1-(1,1-Dimethylethoxycarbonyl)-4-(3-nitro-2-pyridinyl)-1,4diazepine

Following the general procedure of PREPARATION 19 and making non-critical variations but starting with 1-(3-nitro-2-pyridinyl)-1,4diazepine (PREPARATION 21, 7.06 g), the title compound is obtained, NMR (300 MHz, CDCl$_3$) 8.29, 8.05, 6.67, 3.76–3.29, 1.98, 1.34 and 1.29 δ.

Preparation 23

1-(1,1-Dimethylethoxycarbonyl)-4-(3-amino-2-pyridinyl)-1,4-diazepine

Following the general procedure of PREPARATION 52 and making non-critical variations but starting with 1-(1,1-dimethylethoxycarbonyl)-4-(3-nitro-2-pyridinyl)-1,4-diazepine (PREPARATION 22, 6.0 g), title compound is obtained, NMR (300 MHz, CDCl$_3$) 7.75, 6.93, 6.81, 3.86, 3.78, 3.66–3.57, 3.51, 3.36–3.2, 3.21, 1.95, 1.85, 1.48 and 1.47 δ.

Preparation 24

1-(1,1-Dimethylethoxycarbonyl)-4-(3-ethylamino-2-pyridinyl)-1,4-diazepine

Following the general procedure of PREPARATION 1 and making non-critical variations but starting with 1-(1,1-dimethylethoxycarbonyl)-4-(3-amino-2-pyridinyl)-1,4-diazepine (PREPARATION 23, 6.07 g) and acetaldehyde for propional, the title compound is obtained, NMR (300 MHz, CDCl$_3$) 7.65, 6.86, 6.76, 4.25, 4.11, 3.64–3.48, 3.30–3.21, 3.12–3.08, 1.92, 1.83, 1.47, and 1.45 δ.

Preparation 25

1-(3-Ethylamino-2-pyridinyl)-1,4-diazepine (Amine)

Following the general procedure of PREPARATION 4 and making non-critical variations but starting with 1-(1,1-dimethylethoxycarbonyl)-4-(3-ethylamino-2-pyridinyl)-1,4-diazepine (PREPARATION 24, 5.12 g), the title compound is obtained, NMR (300 MHz, CDCl$_3$) 7.66, 6.85, 6.76, 4.17, 3.31–3.26, 3.14–3.01, 1.84 and 1.29 δ.

Preparation 26

1-(1,1-Dimethylethoxycarbonyl)-4-(3-(1-methylethyl)amino-2-pyridinyl)-1,4-diazepine Following the general procedure of PREPARATION 3 and making non-critical variations but starting with 1-(1,1-dimethylethoxycarbonyl)-4-(3-amino-2-pyridinyl)-1,4-diazepine (PREPARATION 23, 18.13 g), the title compound is obtained, NMR (300 MHz, CDCl$_3$) 7.62, 6.85, 6.76, 4.18, 3.63–3.48, 3.28–3.19, 3.07, 1.92, 1.83, 1.46, 1.45 and 1.23 δ.

Preparation 27

1-(3-(1-Methylethyl)amino-2-pyridinyl)-1,4-diazepine (Amine)

Following the general procedure of PREPARATION 4 and making non-critical variations but starting with 1-(1,1-dimethylethoxycarbonyl)-4-(3-(1-methylethyl)-2-pyridinyl)-1,4-diazepine (PREPARATION 26, 15.08 g), the title compound is obtained, NMR (300 MHz, CDCl$_3$) 7.61, 6.82, 6.75, 4.17, 3.50, 3.28–3.22, 3.06–3.01, 2.67, 1.83 and 1.20 δ.

Preparation 28

1-[1,1-Dimethylethoxycarbonyl]-4-[3-(1-methylpropyl)amino-2-pyridinyl]piperazine Following the general procedure of PREPARATION 3 and making non-critical variations but starting with 1-[1,1-dimethylethoxycarbonyl]-4-[(3-amino)-2-pyridinyl] piperazine (International Publication No. WO 88/08424, 1.0 g), 2-butanone (0.27 g) sodium cyanoborohydride (0.23 g), acetic acid (5.1 ml) and methanol, the title compound is obtained, NMR (300 MHz, CDCl$_3$) 7.68, 6.94, 6.86, 4.18, 3.56, 3.33, 3.05, 1.53, 1.47, 1.18 and 0.96 δ.

Preparation 29

1-[3-(1-Methylpropyl)amino)-2-pyridinyl]piperazine

Following the general procedure of PREPARATION 4 and making non-critical variations but starting with 1-[1,1-dimethylethoxycarbonyl]-4-[3-( 1-methylpropyl)amino-2-pyridinyl)piperazine (PREPARATION 28, 1.62 g), trifluoroacetic acid (5.52 g) and 10 ml of methylene chloride, the title compound is obtained, NMR (300 MHz, CDCl$_3$) 7.66, 6.87, 6.78, 4.17, 3.31, 3.06, 2.81, 1.64–1.48, 1.17 and 0.95 δ.

Preparation 30

1-[Benzyloxycarbonyl]-4-[3-(1-ethylpropylamino)-2-pyridinyl]-piperazine

Following the general procedure of PREPARATION 3 and making non-critical variations but starting with 1-[benzyloxycarbonyl]-4-[(3-amino)-2-pyridinyl]piperazine (PREPARATION 33, 10.5 g), 3-pentanone (0.15 g) sodium cyanoborohydride (0.11 g), acetic acid (52.3 ml) and methanol (3.2), the title compound is obtained, NMR (300 MHz, CDCl$_3$) 7.66, 7.38–7.33, 6.90, 6.79, 5.17, 4.21, 3.65, 3.15, 3.04, 1.66–1.46 and 0.93 δ.

Preparation 31

1-[3-(1-Ethylpropyl)amino-2-pyridinyl]piperazine

Starting with 1-[1-benzyloxycarbonyl]-4-[(3-(1-ethylpropylamino)-2-pyridinyl)piperazine (PREPARATION 30, 0.30 g) and using 10% palladium on carbon (30 mg) and ethyl acetate (10 ml), the protecting group is removed to give the title compound, NMR (300 MHz, CDCl$_3$) 7.65, 6.87, 6.78, 4.19, 3.40–3.10, 3.00–2.75, 1.64–1.49, and 0.93 δ.

Preparation 32

1-[Benzyloxycarbonyl]-4-[3-nitro-2-pyridinyl]piperazine 1-(3—Nitro-2-pyridinyl)piperazine is dissolved in 175 ml of methylene chloride and cooled to 0°. Then pyridine is added followed by benzylchloroformate (16.5 ml). The reaction is stirred 1.5 hr, then poured into saturated aqueous sodium bicarbonate and extracted with chloroform, dried over anhydrous sodium sulfate and concentrated in vacuo to afford the title compound, NMR (300 MHz, CDCl$_3$) 8.34, 8.15, 7.38–7.32, 6.81, 5.17, 3.65 and 3.45 δ.

Preparation 33

1-[Benzyloxycarbonyl]-4-[3-amino-2-pyridinyl]piperazine

1-[Benzyloxycarbonyl]-4-[3-nitro-2-pyridinyl]piperazine (PREPARATION 32), is dissolved in dioxane (923 ml) and cooled to 0°. Then aqueous titanium trichloride (20%, 555.3 ml) is added cautiously. After stirring 30 min the reaction is diluted with aqueous sodium hydroxide solution (2N, 1.5 l) and filtered through celite. The filter cake is washed with methanol/chloroform (10/90). The combined organic layers are washed with water, saline, dried and concentrated in vacuo to afford the desired product, NMR (300 MHz, CDCl$_3$) 7.80, 7.38–7.32, 6.99, 6.88, 5.17, 3.67 and 3.12 δ.

Preparation 34

1-[Benzyloxycarbonyl]-4-[3-(2,2,2-trifluoroacetamido)-2-pyridinyl]-piperazine 1-[Benzyloxycarbonyl]-4-[3-amino-2-pyridinyl]piperazine (PREPARATION 33), is dissolved in 50 ml of methylene chloride and triethylamine is added. The reaction is cooled to 0° and trifluoroacetic anhydride is added dropwise. After 30 min, the reaction is poured into saturated aqueous sodium bicarbonate solution and extracted with chloroform, washed with saline, dried over anhydrous sodium sulfate and concentrated in vacuo, NMR (300 MHz, CDCl$_3$) 8.92, 8.54, 8.22, 7.39–7.32, 7.16, 5.17, 3.70 and 3.03 δ.

Preparation 35

1-[3-(2,2,2-Trifluoroacetamido)-2-pyridinyl]piperazine

1-[Benzyloxycarbonyl]-4-[3-(2,2,2-trifluoroacetamido)-2-pyridinyl]piperazine (PREPARATION 34), is dissolved in 70 ml of ethanol and 0.25 g of 10% palladium on carbon is added. The reaction is hydrogenated at 40 psi for 20 hr. Then it is filtered through a pad of celite and concentrated in vacuo to afford the title compound which is used without further purification, NMR (300 MHz, CDCl$_3$) 8.51, 8.21, 7.19, and 3.45–3.47 δ.

Preparation 36

1-[3-(2,2,2-trifluoroethylamino)-2-pyridinyl]piperazine

1-[3-(2,2,2-Trifluoroacetamido)-2-pyridinyl]piperazine (PREPARATION 35), is dissolved in 5 ml of tetrahydrofuran and cooled to 0°. Then 4.84 ml of lithium aluminum hydride solution is added dropwise. After 10 min of stirring at 0°, the reaction is warmed to 20°–25° and stirred 45 min. The reaction is quenched at 0° with the dropwise addition of 0.4 ml of water, 0.6 ml of 10% aqueous sodium hydroxide, and 1 ml of water. The slurry is filtered through celite, washed with 20% methanol/chloroform and concentrated in vacuo to afford the title amine which is used without further purification, NMR (300 MHz, CDCl$_3$) 7.82, 6.97–6.92, 4.86, 3.75, and 3.06–3.01 δ.

Preparation 37

1-[3-(2-Fluoroacetamido)-2-pyridinyl]piperazine

Following the general procedure of PREPARATION 35 and making non-critical variations but starting with 1-benzyloxycarbonyl-4-[3-(2'-fluoroacetamido)-2-pyridinyl]piperazine (2.42 g), 10% palladium on carbon (0.25 g), the title compound is obtained, NMR (300 MHZ, CDCl$_3$) 8.15, 7.97, 7.00, 4.88, 4.73 and 3.13 δ.

Preparation 38

1-[3-(2-Fluoroethylamino)-2-pyridinyl]piperazine

Following the general procedure of PREPARATION 36 and making non-critical variations but starting with 1-[3-(2-fluoroacetamido)-2-pyridinyl]- piperazine (PREPARATION 37, 1.4 g), lithium aluminum hydride (11.76 ml, 1M in tetrahydrofuran), the title compound is obtained.

Preparation 39

1-[1,1-Dimethylethoxycarbonyl]-4-[4-chloro-5-nitro-6-pyrimidyl]-piperazine

A solution of 1-[1,1-dimethylethoxycarbonyl]piperazine (1.88 g) in dichloromethane (30 ml) is added drop by drop over 1.5 hr to a solution of 4,6-dichloro-5-nitropyrimidine (1.94 g) and triethylamine (1.32 g) in dichloromethane (170 ml) at −78°. After stirring an additional hr at −78°, the reaction is diluted with aqueous sodium bicarbonate (10%). The phases are separated, the organic phase is concentrated to a liquid which solidified on standing at 20°–25°. The solid is dissolved in chloroform and flash chromatographed on silica gel eluting with methanol/chloroform (1/99), pooling and concentrating the appropriate fractions gives the title compound, Anal. Calc for C$_{13}$H$_{18}$N$_5$ClO$_4$; MW=343.77: C,45.42; H,5.28; N,20.37; Cl,10.31. Found: C,45.52; H,5.40; N,20.34; Cl,10.36.

Preparation 40

1-[3-(1-Methylethylamino)-2-pyrazinyl]-1,4-diazepine (Amine)

Following the general procedure of PREPARATION 7 and making non-critical variations but starting with homopiperazine (2.46 g) and 2-chloro-3-(1-methylethyl)-aminopyrazine (PREPARATION 6), the title compound is obtained, NMR (300 MHz, CDCl₃) 7.56, 7.34, 4.75, 4.04, 3.28–3.18, 3.00–2.94, 1.79, and 1.15 δ.

Preparation 41

3,5-Dichloro-4-(1-methylethylamino)pyridazine

A solution of 3,4,5-trichloropyridazine (9.2 g) and isopropylamine (16.5 g) in toluene (25 ml) is refluxed for 18 hr. Excess isopropylamine is removed by atmospheric distillation. The residual solution is cooled and diluted with dichloromethane and aqueous sodium hydroxide solution (5%). The phases are separated. The organic phase is washed with water and then with saline. The organic phase is dried over sodium sulfate and concentrated under reduced pressure to give a liquid which contains a mixture of isomeric products. The isomers are separated by flash chromatography on silica gel eluting with ether/hexane (30/70). The appropriate fractions are pooled and concentrated to give the desired isomer, NMR (CDCl₃) 1.33, 4.59, 4.87 and 8.60 δ; CMR (CDCl₃) 24.2, 46.4, 117.1, 139.3, 145.5 and 151.3 δ.

Further elution gives 3,4-dichloro-5-(1-methylethylamino)pyridazine which is recrystallized from ether hexane, NMR (CDCl₃) 1.35, 3.87, 4.80, and 8.55 δ; CMR (CDCl₃) 22.6, 44.7, 116.5, 136.3, 142.5 and 153.4 δ.

Preparation 42

1-[5-Chloro-4-(1-methylethyl)amino-3-pyridazinyl]piperazine

A mixture of 3,5-dichloro-4-(1-methylethyl)aminopyridazine (PREPARATION 41, 1.77 g) and piperazine (2.96 g) in xylene (18 ml) is refluxed for 40 hr. The mixture is cooled and then treated with concentrated hydrochloric acid (8 ml). After further cooling, a precipitate forms and the organic liquid is separated. The aqueous phase is diluted with an excess of a solution of aqueous sodium hydroxide (10%) and then is extracted with chloroform (3×). The combined organic extracts are washed with water, then saline, dried over sodium sulfate, and concentrated to an oil. The crude product is flash chromatographed on silica gel eluting with methanol. The appropriate fractions are pooled and concentrated to give the title compound, NMR (CDCl₃) 1.20, 3.04, 3.18, 4.46, 4.73 and 8.50 δ; CMR (CDCl₃) 24.0, 44.3, 45.9, 50.2, 118.2, 135.8, 148.3 and 155.4 δ.

Preparation 43

3,5-Dichloro-4-(1,1-dimethylethylamino)pyridazine

Following the general procedure of PREPARATION 41 and making non-critical variations but starting with t-butylamine (66.5 ml), and 3,4,5-trichloropyridazine, the title compound is obtained, NMR (300 MHz, CDCl₃) 8.50, 5.09, and 1.55 δ.

Preparation 44

1-[5-Chloro-4-(1,1-dimethylethylamino)-3-pyridazinyl]piperazine

Following the general procedure of PREPARATION 42 and making non-critical variations but starting with 3,5-dichloro-4-(1,1-dimethylethylamino)pyridazine (PREPARATION 43), the title compound is obtained, NMR (300 MHz, CDCl₃) 8.55, 5.04, 3.25, 3.07, and 1.44 δ.

Preparation 45

1-[4-(1,1-Dimethylethylamino)-2-pyridazinyl]piperazine (Amine)

Following the general procedure of PREPARATION 10 and making non-critical variations but starting with 1-[5-chloro-4-(1,1-dimethylethylamino)-3-pyridazinyl]piperazine (PREPARATION 44), and triethylamine (4.6 ml), the title compound is obtained, NMR (300 MHz, CDCl₃) 8.53, 6.79, 5.57, 3.55, and 1.47 δ.

Preparation 46

1-[1,1-Dimethylethoxycarbonyl]-4-[3-(2-propenylamino)-2-pyridinyl]-piperazine

A mixture of 1-[1,1-dimethylethoxycarbonyl]-4-[3-amino-2-pyridinyl]-piperazine (International Publication 88/08424, 2.78 g), 3-bromopropene (1.87 g), anhydrous potassium carbonate (3.3 g) and acetonitrile (100 ml) is refluxed for 36 hr. The mixture is cooled and then diluted with dichloromethane and aqueous potassium carbonate solution. The phases are separated and the organic phase is washed with saline and than concentrated in vacuo. Purification by flash column chromatography (2% methanol/chloroform) provided of the title compound. Capillary GC analysis (HP1 column, initial temperature at 100° for 1 min, then programmed to rise 20° per minute to 250°) gave a peak at 6.06 (96%) minutes.

Preparation 47

1-[3-(2-Propenylamino)-2-pyridinyl]piperazine

Following the procedure of PREPARATION 2 and making non-critical variations but starting with 1-[1,1-dimethylethoxycarbonyl]-4-[3-(2-propenyl)-2-pyridinylamino]piperazine (PREPARATION 46, 0.7 g), the title compound is obtained. TLC analysis (silica gel, eluent: 15% methanol/chloroform, visualization with UV light and iodine vapor) showed one spot, Rf=0.1.

Preparation 48

1-(1,1-Dimethylethoxy)carbonyl-4-methylaminopiperidine

Methylamine hydrochloride (2.36 g) is dissolved in methanol (50 ml) and potassium hydroxide pellets (0.60 g) and N-(1,1-di-methylethoxycarbonyl)-4-piperidone are added. Sodium cyanoborohydride (0.69 g) in methanol (5 ml) is added and the mixture is stirred 2 hrs. Potassium hydroxide pellets (1.96 g) are added to the mixture which is stirred 1 hr and acidified to pH 2 with 6M hydrochloric acid and concentrated. The mixture is diluted with water (50 ml) and extracted with ether (3×80 ml) which is discarded. The aqueous layer is basified to pH 11 with potassium hydroxide pellets, saturated with sodium chloride and extracted with ether (6×80 ml). The combined organic extracts are dried with magnesium sulfate and concentrated to afford an oil which is chromatographed on silica gel with a methanol/chloroform gradient (5–30%). Fractions are pooled on the basis of TLC (R$_f$=0.13, 20% methanol/chloroform) to give the title product, NMR (CDCl₃) 4.04, 2.79, 2.54, 2.46, 2.33, 1.88, 1.46, and 1.26 δ.

Preparation 49

1-(1,1-Dimethylethoxy)carbonyl)-4-(N-methyl-N-(3-nitro-2-pyridinyl)-amino)piperidine Anhydrous potassium carbonate (2.71 g) and 2-chloro-3-nitropyridine (0.93 g) are added to a solution of 1-((1,1-dimethylethoxy)carbonyl)-4-methylaminopiperidine (PREPARATION 48, 1.40 g) in acetonitrile (50 ml). The mixture is stirred 21 hours at 20°–25° and additional 2-chloro-3-nitropyridine (100 mg) and acetonitrile (5 ml) are added. The mixture is stirred 2.8 days, concentrated and dissolved in methylene chloride (175 ml) and water (50 ml). The phases are separated and the organic phase is extracted with water (2×50 ml) and saline (40 ml) and dried over sodium sulfate. Concentration under reduced pressure affords an oil which is chromatographed on silica gel (120 g) eluting with 10% ethyl acetate/hexane. Fractions with $R_f$=0.29 by TLC (silica gel, 25% ethylacetate/hexane) are pooled and concentrated to give the title compound, NMR ($CDCl_3$) 8.29, 8.11, 6.68, 4.62, 4.26, 2.85, 2.67 and 1.48 δ.

Preparation 50

4-(N-methyl-N-(3-nitro-2-pyridinyl)amino) piperidine

Trifluoroacetic acid (13.0 ml) is added to a solution of 1-((1,1-dimethylethoxy)-carbonyl)-4-(N-methyl-N-(3-nitro-2-pyridinyl)amino)piperidine (PREPARATION 49) in methylene chloride (100 ml) with cooling to −78°. The mixture is warmed to 20°–25°, stirred 17 hrs, cooled to 0° and basified to pH 12 with 5% sodium hydroxide. The phases are separated and the aqueous phase is extracted with methylene chloride (2×50 ml). The combined organic phases are dried over sodium sulfate and concentrated to give the title compound, mp 115.5°–117°.

Preparation 52

1-(1,1-Dimethylethoxyl)carbonyl)-4-(N-methyl-N-(3-amino-2-pyridinyl)-amino)piperidine 1-(1,1-Dimethylethoxy)carbonyl)-4-(N-methyl-N-(3-nitro-2-pyridinyl)amino)piperidine (PREPARATION 49, 7.49g) is dissolved in ethanol (135 ml) and palladium on carbon (10%, 0.65 g) is added. The reaction is hydrogenated at 40 psi for 18 hours and filtered through a pad of celites and concentrated under reduced pressure, NMR (d-methanol) 7.54, 6.99, 6.80, 3.90, 2.61, 2.56, 1.63, 1.47 and 1.35 δ.

Preparation 53

1-(1,1-Dimethylethoxyl)carbonyl)-4-(N-methyl-N-(3-(1-methylethylamino-2-pyridinyl)amino) piperidine 1-(1,1-Dimethylethoxy)carbonyl)-4-(N-methyl-N-(3-amino-2-pyridinyl)amino)piperidine (PREPARATION 52) is dissolved in ethanol (137 ml) and cooled to 12)°. Glacial acetic acid (39.3 ml) and acetone (2.22 ml) are added. After 15 min sodium cyarboborohydride (4.99 g) is added and the reaction is warmed to 20°–25°. Since reaction did not appear complete by TLC (ethyl acetate/hexane, 75/25), a total of 3.5 equivalents of acetone and acetic acid are added over a 24 hour period. The reaction is poured into water, extracted with chloroform, dried over sodium sulfate and concentrated under reduced pressure. Flash column chromatography eluting with ethyl acetate/hexane (20/80), pooling the appropriate fractions and concentrating gives the title compound, NMR (d-methanol) 7.47, 6.90, 3.92, 3.51, 2.71, 2.51, 1.35, 1.61 and 1.11 δ.

Preparation 54

4-(N-Methyl-N-(3-(1-methylethylamino)-2-pyridinyl)amino)-piperidine

Following the procedure of PREPARATION 50, but substituting 1-(1,1-dimethylethoxy)carbonyl)-4-(N-methyl-N-(3-(1-Methylethylamino-2-pyridinyl)amino)piperidine (PREPARATION 53) for 1-(1,1-dimethylethoxy)carbonyl)-4-(N-methyl-N-(3-nitro-2-pyrimidinyl)amino)piperidine and starting the reaction at 0°, the title compound is obtained, NMR (d-methanol) 7.47, 6.89, 3.50, 3.05, 2.93, 2.52, 2.42, 1.62, 1.45 and 1.11 δ.

Preparation 55

1-[5—Nitroindolyl-2-carbonyl]-4-[N-methyl-N-(3-(1-methylethylamino)-2-pyridinyl)amino]piperidine A mixture of 5-nitroindole-2-carboxylic acid (2.39 g) and 1-(3-dimethylaminopropyl)-3-ethylcarbodiimide hydrochloride (2.33 g) in dry THF (600 ml) are stirred with a mechanical stirrer under nitrogen at 20°–25° for 45 min. To this is added a solution of 4-(N-methyl-N-(3-(1-methylethylamino)-2-pyridinyl)amino)-piperidine (PREPARATION 54, 2.88 g) in dry THF (20 ml) and the mixture is stirred for 1.8 days. The supernatant liquid is removed, concentrated to dryness, and diluted with methylene chloride (75 ml) and water (25 ml). The layers are separated and the organic phase is washed with saturated aqueous sodium bicarbonate (30 ml) and saline and dried over sodium sulfate. Removal of solvent under reduced pressure gives a solid which is chromatographed on silica gel (70–230 mesh, 400 g), eluting with a gradient of methanol/chloroform (0.5/99.5–5/95). Pooling of the appropriate fractions, having an $R_f$ of about 0.34 by TLC (methanol/chloroform 5/95) and removal of solvent under reduced pressure gives the title compound, mp 204–206°.

Preparation 56

1-[5-Aminoindolyl-2-carbonyl]-4-[N-methyl-N-(3-(1-methylethylamino)-2-pyridinyl)amino]-piperidine (VII)

Palladium on carbon (10%, 200 mg) is added to a mixture of 1-[5-nitroindolyl-2-carbonyl]-4-[N-methyl-N-(3-(1-methylethylamino)-2-pyridinyl)amino]piperidine (PREPARATION 55, 400 mg) in DMF/methanol under nitrogen. The mixture is put under a hydrogen atmosphere (balloon), stirred for 5 hrs, and the catalyst is filtered off through a pad of diatamacious earth. The filtrate is concentrated under reduced pressure to give the title compound.

Preparation 57

1-Methyl 4-methoxy-α-azidocinnamate p-Methoxybenzaldehyde (5.0 g) and methyl azidoacetate (16.9 g) are dissolved in 125 ml of methanol and cooled to −10° (ice-acetone bath). Then sodium methoxide (7.93 g, 25% in methanol) is added dropwise such that the temperature does not rise above −5°. After 2 hr the cooling bath is removed and the reaction is warmed to 20°–25° while being monitored by TLC. When no starting material remained, the reaction is diluted with ether and saturated ammonium chloride. After extracting with ether the organic layers are washed with ammonium chloride, saline, dried over anhydrous sodium sulfate and concentrated under reduced pressure. The concentrate is purified by flash column chromatography eluting with ethyl acetate/hexane (1/99) to ethyl acetate/hexane (10/90). The appropriate fractions are pooled and concentrated to give the title compound, NMR (300 MHz, $CDCl_3$) 7.80–7.76, 6.92–6.87, 3.88 and 3.79 δ.

Preparation 58

Methyl 6-Methoxyindole-2-carboxylate

Toluene (185 ml) is added to methyl 4-methoxy-α-azidocinnamate (PREPARATION 61, 7.73 g) and the reaction is brought to reflux and maintained at reflux for 3 hr. Then the reaction is concentrated under reduced pressure and triturated with hexane. The solids are filtered and dried under reduced pressure to give the title indole, HRMS Calcd. for $C_{11}H_{11}NO_3$: 205.0739, found: 205.0736; NMR (300 MHz, $CDCl_3$) 8.75, 7.47, 7.11, 6.76–6.73, 3.86, 3.79 δ.

Preparation 59

6-Methoxyindole-2-carboxylic acid (I)

Methyl 6-methoxyindole-2-carboxylate (PREPARATION 62, 5.71 g) is dissolved in 70 ml of dioxane and 7 ml of water and 1.87 g of crushed potassium hydroxide are added. The reaction is heated to 50° and stirred 1.5 hr. The reaction mixture is acidified to pH 4–5 and extracted several times with methanol/chloroform (10/90). The organic layers are combined and dried over anhydrous magnesium sulfate and concentrated under reduced pressure to give the title acid, NMR (300 MHz, d4-$CD_3OD$) 7.47, 7.08, 6.90, 6.72 and 3.82 δ.

Preparation 60

Methyl 4-nitro-α-azidocinnamate

Following the general procedure of PREPARATION 57 and making non-critical variations but starting with p-nitrobenzaldehyde (10 g) and methyl azidoacetate (30.4 g), the title compound is obtained, NMR 8.34, 8.07, 7.02, and 4.07 δ.

Preparation 61

Methyl 6-nitroindole-2-carboxylate

Following the general procedure of PREPARATION 58 and making non-critical variations but starting with methyl 4-nitro-β-azidocinnamate (PREPARATION 60, 6.75 g), the title compound is obtained, NMR (300 MHz, $CD_3OD$) 8.30, 7.87, 7.72, 7.18, and 3.86 δ.

Preparation 62

6-Nitroindole-2-carboxylic acid (I)

Following the general procedure of PREPARATION 59 and making non-critical variations but starting with methyl 6-nitroindole-2-carboxylate (PREPARATION 61), the title compound is obtained.

Preparation 64

1-[6-Nitroindoyl-2-carbonyl]-4-[3-(1-methylethylamino)-2-pyridinyl]piperazine

Following the general procedure of PREPARATION 55 and making non-critical variations but starting with 6-nitroindole-2-carboxylic acid (PREPARATION 62) and 1-[3-(1-methylethylamino)-2-pyridinyl]piperazine (PREPARATION 4), the title compound is obtained.

Preparation 65

1-[1,1-Dimethylethoxycarbonyl]-4-[3-(1,1-dimethylprop-2-ynylamino)-2-pyridinyl]piperazine To a mixture of 1-[1,1-dimethylethoxycarbonyl]-4-[3-amino-2-pyridinyl]piperazine (International Publication No. WO 88/08424, 5.40 g), cuprous chloride (1.00 g), copper powder (1.00 g), and dry dimethylformamide (25 ml) under nitrogen at 0° is added a solution of 3-chloro-3-methyl-1-butyne (2.00 g) in dry dimethylformamide (5 ml) in 4 portions over 15 min. The resulting mixture is then stirred at 20°–25° for 16 hrs, concentrated, and diluted with methylene chloride (75 ml) and water (20 ml). The layers are separated and the aqueous phase is extracted with methylene chloride (25 ml). The combined organic phase is washed with saline (20 ml), dried over anhydrous magnesium sulfate, and concentrated under reduced pressure to give a residue which is chromatographed on silica gel (70–230 mesh, 500 g), eluting with a gradient of ethyl acetate/hexane (10/90–20/80). Pooling of fractions giving an $R_f$=0.31 (ethyl acetate/hexane, 25/75) and removal of solvent under reduced pressure gives the title compound, NMR ($CDCl_3$) 7.75, 7.47, 6.94, 4.61, 3.56, 3.00, 2.39, 1.64 and 1.48 δ.

Preparation 66

1-[1,1-Dimethylethoxycarbonyl]-4-[3-(1,1-dimethylpropylamino)-2-pyridinyl]piperazine To a solution of 1-[1,1-dimethylethoxycarbonyl]-4-[3-(1,1-dimethylprop-2-ynylamino)-2-pyridinyl]piperazine (PREPARATION 65, 1.00 g) in absolute ethanol (20 ml) under nitrogen is added wet Raney Nickel (650 mg). The mixture is put under a hydrogen atmosphere at 40 psi (Parr) for 20 hr, filtered through a pad of celite, and concentrated. The residue is then taken up in methylene chloride (40 ml), washed with saline (10 ml), dried over sodium sulfate, and concentrated under reduced pressure to give the title compound, NMR ($CDCl_3$) 7.64, 7.03, 6.85, 4.56, 3.56, 2.97, 1.71, 1.48, 1.33 and 0.88.

Preparation 67

1-[5-Nitroindole-2-carbonyl]-4-[3-(1,1-dimethylpropylamino)-2-pyridinyl]piperazine To a solution of 1-[1,1-dimethylethoxycarbonyl]-4-[3-(1,1-dimethylpropylamino)-2-pyridinyl]piperazine (PREPARATION 66, 4.99 g) in methylene chloride (75 ml) under nitrogen at 0° is added trifluoroacetic acid (14.3 ml) over 1 min. The resulting mixture is warmed to 20°–25°, stirred for 15 hrs, and then added to a solution of sodium hydroxide (7.44 g) in water (175 ml) at 0°. The layers are separated, the aqueous phase is extracted with methylene chloride (3×70ml), and the combined organic layer is washed with saline (60 ml), dried over sodium sulfate, and concentrated under reduced pressure to give the unprotected intermediate ($R_f$=0.14, TLC, methanol/chloroform, 10/90). In a flame-dried flask under nitrogen, 5-nitroindole-2-carboxylic acid (2.13 g) and 1,1'-carbonyldiimidazole (1.75 g) are dissolved in dry tetrahydrofuran and stirred for 3 hrs at 20°–25°. Then a solution of the intermediate (2.57 g) in dry tetrahydrofuran (3ml) is added and the resulting mixture is stirred for 1.8 days. The reaction mixture is filtered to give the title compound, NMR (dimethylsulfoxide-de) 12.41, 8.65, 8.09, 7.58, 7.16, 7.11, 6.91, 4.57, 3.93, 3.00, 1.71, 1.31 and 0.84. The filtrate is concentrated and is triturated with cold methanol to give an additional mount of the title compound.

Preparation 68

1-(1,1-Dimethylethoxycarbonyl)-4-(1,1-dimethylprop-2-ynyl)piperazine

To a mixture of 1-(1,1-dimethylethoxycarbonyl) piperazine (3.29 g), copper powder (20 mg), cuprous chloride (20 mg), ether (4 ml), and water (1 ml) under nitrogen at 0° is added a solution of 3-chloro-3-methyl-1-butyne in ether (1 ml) in 4 portions over 15 min. The mixture is stirred at 20°–25° for 2 hr, diluted with ether (25 ml) and water (10 ml), and the layers are separated. The aqueous layer is extracted with ether (3×25 ml), and the combined organic layer is washed with saline (25 ml), dried over anhydrous magnesium sulfate, and concentrated under reduced pressure to give a solid which is then chromatographed on silica gel (70–230, 100 g), eluting with ethyl acetate/hexane (25/75). Pooling of fractions giving an $R_f$=0.48 by TLC (ethyl acetate/hexane, 50/50) and removal of solvent under reduced pressure gives the title compound, mp 105.5°–107°.

Preparation 69

1-(1,1-Dimethylethoxycarbonyl)-4-(1,1-dimethylpropyl)piperazine

A flask is charged with platinum oxide (250 mg) and absolute ethanol (20 ml) and is stirred under a hydrogen atmosphere (balloon) for 1 hr. Then a solution of 1-(1,1-dimethylethoxycarbonyl)-4-(1,1-dimethylprop-2-ynyl) piperazine (PREPARATION 68, 1.77 g) in absolute ethanol (20 ml) is added, and the mixture is stirred under hydrogen (balloon) for 4 hr, filtered, and concentrated. The residue is chromatographed on silica gel (70–230 mesh, 80 g), eluting with ethyl acetate/hexane (25/75), and the appropriate fractions ($R_f$=0.32, TLC, ethyl acetate/hexane, 25/75) are pooled and concentrated to give the title compound, NMR (CDCl$_3$) 3.38, 2.46, 1.46–1.38, 0.97 and 0.84.

Preparation 70

1-(1,1-Dimethylpropyl)piperazine

Following the general procedure of PREPARATION 50, but substituting 1-(1,1-dimethylethoxycarbonyl)-4-(1,1-dimethylpropyl)piperazine (PREPARATION 69) for 1-[1,1-dimethylethoxycarbonyl]-4-[N-methyl-N-(3-nitro-2-pyridinyl)amino]]piperidine and starting the reaction at 0°, the title compound is obtained, NMR (CDCl$_3$) 2.87, 2.50, 1.91, 1.42, 0.97 and 0.84.

Preparation 71

1-[1,1-Dimethylethoxycarbonyl]-4-[N-methyl-N-(3-(1,1-dimethylprop-2-ynylamino)-2-pyridinyl)amino] piperidine Following the general procedure of EXAMPLE 65, but substituting 1-[1,1-dimethylethoxycarbonyl]-4-[N-methyl-N-(3-amino-2-pyridinyl)amino]piperidine (PREPARATION 52) for 1-[1,1-dimethylethoxycarbonyl]-4-[3-amino-2-pyridinyl]piperazine and working up the reaction after 2 hrs, the title compound is obtained, NMR (CDCl$_3$) 7.79, 7.51, 6.95, 4.92, 4.05, 3.19, 2.75, 2.61, 2.38, 1.75, 1.62, 1.49 and 1.45 δ.

Preparation 72

1-[1,1-Dimethylethoxycarbonyl]-4-[N-methyl-N-(3-(1,1-dimethylpropylamino)-2-pyridinyl)amino] piperidine Following the general procedure of EXAMPLE 66, but substituting 1-[1,1-dimethylethoxycarbonyl]-4-[N-methyl-N-(3-(1,1-dimethylprop-2-ynylamino)-2-pyridinyl)amino] piperidine (PREPARATION 71 ) for 1-[1,1-dimethylethoxycarbonyl]-4-[3-(1,1-dimethylprop-2-ynylamino)-2-pyridinyl]piperazine, the crude product is obtained. This is then chromatographed on silica gel (70–230 mesh, 250 g), eluting with a gradient of ethyl acetate/hexane (10/90–35/65), and the appropriate fractions are pooled and concentrated to give the title compound, NMR (CDCl$_3$) 7.67, 7.04, 6.87, 4.87, 4.04, 3.20, 2.76, 2.61, 1.71, 1.50, 1.45, 1.31 and 0.86 δ.

Preparation 73

4-[N-Methyl-N-(3-(1,1-dimethylpropylamino)-2-pyridinyl)amino]-piperidine

Following the general procedure of PREPARATION 50, but substituting 1-[1,1-dimethylethoxycarbonyl]-4-[N-methyl-N-(3-(1,1-dimethylpropylamino)-2-pyridinyl) amino]piperidine (PREPARATION 72) for 1-[1,1-dimethylethoxycarbonyl]-4-[N-methyl-N-(3-nitro-2-pyridinyl)amino]piperidine, starting the reaction at 0°, and working up the reaction after 1.5 hr, the title compound is obtained, NMR (CDCl$_3$) 7.66, 7.02, 6.84, 4.86, 3.39, 3.13, 2.63, 1.81–1.52, 1.31 and 0.87 δ.

Preparation 74

1-[5-Nitroindole-2-carbonyl]-4-[N-methyl-N-(3-(1,1-dimethylpropyl amino)-2-pyridinyl)amino] piperidine Under nitrogen 5-nitroindole-2-carboxylic acid (977 mg) and 1,1'-carbonyldiimidazole (807 mg) are dissolved in dry tetrahydrofuran (25 ml) and the mixture is stirred at 20°–25° for 2 hr. A solution of 4-[N-methyl-N-(3-(1,1-dimethylpropylamino)-2-pyridinyl)amino]piperidine (PREPARATION 73, 1.31 g) in dry tetrahydrofuran is then added, and the resulting mixture is stirred for 18 hr and filtered. The filtrate is concentrated, diluted with methylene chloride (75 ml), washed with water and saline (20 ml), dried over sodium sulfate, and concentrated under reduced pressure to give a solid which is chromatographed on silica gel (70–230 mesh, 200 g), eluting with a gradient of ethyl acetate/hexane (50/50–90/10). Pooling of fractions giving an $R_f$=0.08 by TLC (ethyl acetate/hexane, 50/50) and removal of solvent under reduced pressure gives the title compound, mp 205.5°–207.5°.

Preparation 75

1-[5-Aminoindole-2-carbonyl]-4-[N-methyl-N-(3-(1,1-dimethylpropylamino)-2-pyridinyl)amino] piperidine Following the general procedure of EXAMPLE 41, but substituting 1-[5-nitroindole-2-carbonyl]-4-[N-methyl-N-(3-(1,1-dimethylpropylamino)-2-pyridinyl)amino] piperidine (PREPARATION 74) for 1-[5-nitroindole-2-carbonyl]-4-[3-(1,1-dimethylpropylamino)-2-pyridinyl] piperazine and using dimethylformamide/methanol (25/75) as solvent, the title compound is obtained, NMR (CDCl$_3$) 9.95, 7.69, 7.20, 7.05, 6.88, 6.71, 6.55, 4.91, 4.64, 3.86, 3.40, 3.11, 2.62, 1.91, 1.63, 1.31 and 0.86 δ.

Preparation 76

1-(1,1-Dimethylethoxycarbonyl)-cis-3,5-dimethylpiperazine

Di-tert-butyldicarbonate (5.42 g) in dry methylene chloride (20 ml) is added to a solution of cis-2,6-dimethylpiperazine in dry methylene chloride (70 ml) over one hour. The mixture is stirred an additional 30 min, washed with water and saline, dried over sodium sulfate and concentrated to give the title compound, NMR (chloroform-d) 3.95, 2.77, 2.32, 1.46, 1.06 δ.

Preparation 77 cis 3,4,5-Trimethylpiperazine

To a solution of 1-(1,1, dimethylethoxycarbonyl)-cis-3,5-dimethylpiperazine (PREPARATION 76, 4.28 g) in dioxane (100 ml) is added 1M sodium dihydrogen phosphite (100 ml, made by mixing equal volumes of 2M sodium hydroxide and 2M phosphorous acid) followed by the addition of formalin solution (37%, 16 ml). The mixture is heated at 65° for 2.5 hr and extracted with methylene chloride. The organic phase is washed with water and saline, dried over sodium sulfate and concentrated to ca. 50 ml. The remaining methylene chloride and dioxane are removed by distillation leaving 4.3 g of residue in the distillation flask. This material is dissolved in methylene chloride (40 ml), cooled to 0°, and trifluoroacetic acid (14.5 ml) is added. The mixture is stirred for 1.25 hr and sodium hydroxide (11.3 g) in water (30 ml) is added. The phases are separated and the aqueous phase is extracted with additional methylene chloride. The total combined organics are dried over magnesium sulfate and concentrated by distillation to give a mixture of the title compound and residual starting material. On standing the mixture partially crystallizes. Filtration and washing with ethyl ether gives the title compound, NMR (chloroform-d) 3.09, 2.67, 2.39, 1.16 δ.

Preparation 78

4-(2-(2-Methoxyethoxy)ethoxy)benzaldehyde

Following the general procedure of EXAMPLE 1, and making non-critical variations but substituting 1-bromo-2-(2-methoxyethoxy)ethane (Aldrich) for 2-[2-(2-chloroethoxy)ethoxy]ethanol, the title compound is obtained, mp 44°–47°; NMR (300 MHz, CDCl$_3$) 9.78, 7.72, 6.92, 4.12, 3.79, 3.63, 3.48, 3.29 δ.

Preparation 79

Methyl 4-(2-(2-methoxyethoxy)ethoxy)-α-azidocinnamate

Following the general procedure of EXAMPLE 2, and making non-critical variations but substituting 4-(2-(2-methoxyethoxy)ethoxy)benzaldehyde (PREPARATION 78) for 4-[(2-(2-hydroxyethoxy)ethoxy)ethoxy]benzaldehyde, the title compound is obtained, NMR (300 MHz, CD$_3$OD) 7.68, 6.85, 6.78, 4.05, 3.78, 3.72, 3.61, 3.48, 3.28 δ.

Preparation 80

Methyl 6-(2-(2-methoxyethoxy)ethoxy)indole-2-carboxylate

Following the general procedure of EXAMPLE 3, and making non-critical variations but substituting 4-(2-(2-methoxyethoxy)ethoxy)-α-azidocinnamate6 (PREPARATION 79) for 4-[(2-(2-hydroxyethoxy)ethoxy)ethoxy]-α-azidocinnamate, the title compound is obtained, NMR (300 MHz, CD$_3$OD) 7.59, 7.20, 7.02, 6.87, 4.25, 4.00, 3.96, 3.80, 3.67 and 3.47.

Preparation 81

6-(2-(2-Methoxyethoxy)ethoxy)indole-2-carboxylic acid

Following the general procedure of EXAMPLE 4, and making non-critical variations but substituting methyl 6-(2-(2-methoxyethoxy)ethoxy)indole-2-carboxylate (PREPARATION 79) for methyl 6-[(2-(2-hydroxyethoxy)ethoxy)ethoxy]indole-2-carboxylate, the title compound is obtained, mp 99°–102°.

Preparation 82

Ethyl 5-[(3-chloropropyl)sulfonamido]indole-2-carboxylate

Ethyl 5-aminoindole-2-carboxylate (2.0 g) and pyridine (0.82 ml) are dissolved in 15 ml of methylene chloride and 10 ml of THF. Then the reaction is cooled to 0° and 3-chloropropanesulfonyl chloride (1.25 ml) is added and the reaction is allowed to slowly warm to 20°–25° and stir for 16 hr. Then the reaction is diluted with chloroform, washed with saturated aqueous sodium bicarbonate and saline. The organic layers are dried over anhydrous sodium sulfate and concentrated under reduced pressure. The product is dissolved in ethyl acetate and filtered through a plug of silica gel and crystallized from methanol, mp 195°–196°.

Preparation 83

Ethyl 5-[(3-(piperadin-1-yl)propyl)sulfonamido]indole-2-carboxylate

Ethyl 5-[(3-chloropropyl)sulfonamido]indole-2-carboxylate (PREPARATION 82, 2.3 g) is dissolved in acetonitrile (10 ml) and piperadine (27 ml). Solid sodium iodide (1.0 g) is added and the reaction is stirred overnight at 20°–25°. The reaction is diluted with methylene chloride, washed with saturated aqueous sodium bicarbonate, dried over anhydrous sodium sulfate and concentrated under reduced pressure. Purification by flash column chromatography, eluting with a gradient of 5% methanol/methylene chloride to 10% methanol/methylene chloride, pooling and concentration of the appropriate fractions gives the title compound, NMR (300 MHz, d$_4$-CD$_3$OD) 7.45, 7.32, 7.12, 7.03, 4.28, 2.96, 2.28, 1.18, 1.42, 1.33 and 1.30.

Preparation 84

5-[(3-(Piperadin-1-yl)propyl)sulfonamido]indole-2-carboxylic acid

Ethyl 5-[(3-(piperadin-1-yl)propyl)sulfonamido]indole-2- carboxylate (PREPARATION 83, 1.63 g) is dissolved in 10 ml of dioxane and 5 ml of water. Then 0.59 g of solid potassium hydroxide pellets are added and the reaction is stirred at 20°–25° for 24 hr. Then 8.91 ml of 1N hydrochloric acid is added after diluting the reaction with 100 ml of water. The mixture is extracted with n-butanol (3×50 ml) and the organic layer is separated and evaporated under reduced pressure to provide the title compound, NMR (300 MHz, d$_6$-DMSO) 7.37, 7.27, 7.00, 6.90, 2.91, 2.25, 1.75, 1.31, (peak at 4.3 ppm obscured by DMSO).

Preparation 85

1-[5-((1-Carbobenzyloxy)piperadin-4-yl)amido) indolyl-2-carbonyl]-4-[3-1-methhylethylamino)-2-pyridinyl]piperazine 1-[5-Aminoindolyl-2-carbonyl]-4-[3-(1-methylethylamino)-2-pyridinyl]piperazine (EXAMPLE 7, 0.5 g) and 1-benzyloxycarbonylpiperadine-4-carboxylic acid (0.36 g) is dissolved in 2.6 ml of DMP and 0.278 g of EDC is added. The reaction is stirred at 20°–25° overnight, diluted with chloroform, extracted with saturated aqueous sodium bicarbonate, water, saline, dried over anhydrous sodium sulfate and concentrated under reduced pressure. Purification by flash column chromatography, eluting with methanol/chloroform (2.5/97.5), pooling and concentrating the appropriate fractions gives the title compound, mp 138°–142°, NMR (300 MHz, CD$_3$OD) 8.05, 7.72, 7.55–7.40, 7.14, 6.97, 5.28, 4.38, 4.18, 3.79, 3.45, 3.25, 3.02, 2.76, 2.05, 1.86, 1.40.

Preparation 86

1-[5-(3-Chloropropyl)sulfonamidoindolyl-2-carbonyl]-4-[3-(1-methhylethylamino)-2-pyridinyl] piperazine 1-[5-Aminoindolyl-2-carbonyl]-4-[3-(1-methylethylamino)-2-pyridinyl]piperazine (EXAMPLE 7, 2.0 g) is dissolved in 17.6 ml of pyridine and cooled to 0°. Then 3-chloropropanesulfonyl chloride (1.28 ml) is added and the reaction is allowed to warm to 20°–25° and stirred 8 hr. The reaction is diluted with chloroform, washed with saturated aqueous sodium bicarbonate, water, saline, dried over anhydrous sodium sulfate and concentrated under reduced pressure. Purification by flash column chromatography eluting with a gradient of 50/50 ethyl acetate/hexane to 100% ethyl acetate, pooling and concentrating of the appropriate fractions gives the title compound, mp 219°–221°.

Preparation 87

3-Methoxy-4-[2-(1-morpholinyl)benzaldehyde

Vanillin (10.0 g) and 4-(2-chloroethyl)morpholine hydrochloride (19.56 g) are dissolved in 219 ml of DMP and solid potassium carbonate (29 g) is added. The reaction is refluxed for 24 hr, cooled to 20°–25° and the DMF is removed under reduced pressure. The remainder of the reaction is dissolved in ethyl acetate and washed with 1N aqueous sodium hydroxide, saline, dried over anhydrous sodium sulfate and concentrated under reduced pressure. Purification by flash column chromatography eluting with methanol/ethyl acetate (2/98), pooling and concentrating the appropriate fractions gives the title compound, NMR (300 MHz, CDCl$_3$) 9.76, 7.36, 7.34, 6.93, 4.26, 3.84, 3.73, 2.92, 2.66.

Preparation 88

Methyl 3-methoxy-4-[2-(1-morpholinyl)ethoxy]-α-azidocinnamate (IV)

Following the general procedure of EXAMPLE 2, and making non-critical variations but substituting 3-methoxy-4-[2-(1-morpholinyl)benzaldehyde (PREPARATION 87) for 4-[(2-(2-hydroxyethoxy)ethoxy)ethoxy]benzaldehyde, the title compound is obtained, NMR (300 MHz, CDCl$_3$) 7.29, 7.11, 6.67, 6.65, 4.05, 3.67, 3.58, 2.75, 2.51.

Preparation 89

Methyl 5-methoxy-6-[2-(1-morpholinyl)ethoxy]-indole-2-carboxylate (V)

Following the general procedure of EXAMPLE 3, and making non-critical variations but substituting methyl 3-methoxy-4-[2-(1-morpholinyl)ethoxy]-α-azidocinnamate (PREPARATION 88) for methyl 6-[(2-(2- hydroxyethoxy)ethoxy)ethoxy]-α-azidocinnamate and toluene for xylene, the title compound is obtained, mp 123°–124°, NMR (300 MHz, CD$_3$OD) 6.99, 6.96, 6.85, 4.06, 3.78, 3.74, 3.61, 2.74, 2.54.

Preparation 90

5-Methoxy-6-[2-(1-morpholinyl)ethoxy]indole-2-carboxylic acid (VI)

Following the general procedure of EXAMPLE 4, and making non-critical variations but substituting methyl 5-methoxy-6-[2-(1-morpholinyl)ethoxy]indole-2-carboxylate (PREPARATION 89) for methyl 6-[(2-(2-hydroxyethoxy)ethoxy)ethoxy]indole-2-carboxylate, the title compound is obtained, mp>350° but turned black at 237°; NMR (300 MHz, CD$_3$OD) 7.48, 7.03, 6.90, 6.70, 4.09, 3.95, 3.75, 3.62, 3.54, 3.00, 2.76, 2.56, 1.16; CMR (75 MHz, CD$_3$OD) 165.2, 151.4, 149.6, 147.8, 138.7, 135.4, 133.1, 129.4, 122.4, 122.1, 118.9, 105.9, 104.5, 97.7, 68.4, 67.8, 58.9, 57.8, 55.4 50.6, 45.0, 23.0 δ.

Preparation 91

4-[2-(1-Piperadinyl)ethoxy]benzaldehyde

4—Hydroxybenzaldehyde (25.0 g) and 4-(2-chloroethyl) piperadine hydrochloride (60.38 g) are dissolved in DMF (650 ml) and solid potassium carbonate (45 g) is added. The reaction is refluxed for 24 hr, cooled to 20°–25° and the DMF is removed under reduced pressure. The remainder of the reaction is dissolved in chloroform and washed with 1N aqueous sodium hydroxide, saline, dried over anhydrous sodium sulfate and concentrated under reduced pressure. Purification by flash column chromatography eluting with a gradient of 50% ethyl acetate/hexane to 5% methanol/ethyl acetate, pooling and concentrating the appropriate fractions gives the title compound, NMR (300 MHz, CDCl$_3$) 9.75, 7.69, 6.87, 4.10, 2.73, 2.45, 1.52, 1.36 δ.

Preparation 92

Methyl 4-[2-(1-piperadinyl)ethoxy]-α-azidocinnamate (IV)

Following the general procedure of EXAMPLE 2, and making non-critical variations but substituting 4-[2-(1-piperadinyl)benzaldehyde (PREPARATION 91) for 4-[(2-(2-hydroxyethoxy)-ethoxy)ethoxy]benzaldehyde, the title compound is obtained, NMR (300 MHz, CDCl$_3$) 7.75, 6.89, 6.85, 4.16, 3.87, 2.82, 2.56, 1.63, 1.45 δ.

Preparation 93

Methyl 6-[2-(1-piperadinyl)ethoxy]indole-2-carboxylate (V)

Following the general procedure of EXAMPLE 3, and making non-critical variations but substituting methyl 4-[2-(1-piperadinyl)ethoxy]-α-azidocinnamate (PREPARATION 92) for methyl 6-[(2-(2-hydroxyethoxy)ethoxy)ethoxy]-α-azidocinnamate, the title compound is obtained, NMR (300 MHz, CD$_3$OD) 7.40, 7.00, 6.81, 6.65, 4.05, 3.79, 2.71, 2.48, 1.53, 1.39 δ.

Preparation 94

6-[2-(1-Piperadinyl)ethoxy]indole-2-carboxylic acid (VI)

Following the general procedure of EXAMPLE 4, and making non-critical variations but substituting methyl 6-[2-(1-piperadinyl)ethoxy]indole-2-carboxylate (PREPARATION 93) for methyl 6-[(2-(2-hydroxyethoxy)ethoxy)ethoxy]indole-2-carboxylate, the title compound is obtained, NMR (300 MHz, CD$_3$OD) 7.40, 6.96, 6.88, 6.70, 4.28, 3.20, 3.18, 1.78, 1.58, 1.65 δ.

Preparation 95

1-Benzyl-4-[3-(1-cyano-1-methylethylamino) pyridyl]piperazine

The 1-[5-Aminoindolyl-2-carbonyl]-4-[3-(1-methylethylamino)-2-pyridinyl]piperazine (EXAMPLE 7, 11.68 g, 43.51 mmol) is dissolved in 130 ml methanol and 130 ml acetic acid. Acetone (25.6 ml, 348.1 mmol) and trimethylsilylcyanide (46.4 ml, 348.1 mmol) are added and the mixture is stirred twenty hours. The solution is poured into cold aqueous sodium hydroxide solution, stirring vigorously, to give a basic solution. The aqueous solution is then extracted with ethyl acetate, the organic extract is washed with saline, dried over sodium sulfate and evaporated to dryness to give an oily residue of 12.6 g. Chromatography on a 400 g silica gel column with a step gradient of ethyl acetate/hexane (2/3 to 3/2, v/v), pooling and concentrating the appropriate fractions gives the title compound, NMR (300 MHz, CD$_3$OD) 7.65, 7.29–7.17, 6.96–6.92, 3.51, 2.98, 2.55, 1.14 δ.

Preparation 96

1-Benzyl-4-[3-(1,1-dimethylethylamino)pyridyl] piperazine

Methyllithium (61 ml, 85 mmol) as a 1.4M solution in diethyl ether is added to 30 ml tetrahydrofuran and cooled to −78°. 1-Benzyl-4-[3-(1-cyano-1-methylethylamino)pyridyl]-piperazine (PREPARATION 95, 7.14 g, 21.28 mmol), dissolved in 30 ml cooled tetrahydrofuran, is cannulated into the methyllithium solution, rinsing in with 10 ml THF. The reaction is stirred at −78° and allowed to warm to 20°–25° overnight. The reaction is cautiously quenched with water, then extracted from water with methylene chloride. The extract is dried over sodium sulfate and concentrated. The concentrate is chromatographed on a 500 g silica gel column, eluting with ethyl acetate/hexane (2/3, v/v), the appropriate fractions are pooled and concentrated to give the title compound, NMR (300 MHz, CD$_3$OD) 7.44, 7.43–7.07, 6.84–6.80, 3.49, 2.92, 2.52, 1.28 δ.

Preparation 97

1-[3-(1,1-Dimethylethylamino)pyridyl]piperazine

1-Benzyl-4-[3-(1,1-dimethylethylamino)pyridyl] piperazine (PREPARATION 96, 4.25 g, 13.10 mmol) is dissolved in 100 ml ethanol. Palladium (10% on carbon, 1.0 g) is added and the solution hydrogenated at 40 psi hydrogen gas. The mixture is filtered and concentrated to give the title compound, NMR (300 MHz, CD$_3$OD) 7.53, 7.19, 6.93, 2.95, 1.39 δ.

Preparation 98

1-[5—Nitroindolyl-2-carbonyl]-4-[3-(1,1-dimethylethylamino)-2-pyridyl]-piperazine Following the general procedure of EXAMPLE 6, and making non-critical variations but substituting 1-[3-(1,1-dimethylethylamino)-2-pyridyl]piperazine (PREPARATION 97) for 1-[3-(1-methylethylamino)-2-pyridinyl]piperazine, the title compound is obtained, mp 278° (dec.).

Preparation 99

1-[5-Aminoindolyl-2-carbonyl]-4-[3-(1,1-dimethylethylamino)-2-pyridyl]-piperazine Following the general procedure of EXAMPLE 7, and making non-critical variations but substituting 1-[5-nitroindolyl-2-carbonyl]-4-[3-(1,1-dimethylethylamino)-2-pyridyl]piperazine (PREPARATION 98) for 1-[5-nitroindolyl-2-carbonyl]-4-[3-(1-methylethylamino)-2-pyridyl]-piperazine, the title compound is obtained, NMR (CDCl$_3$) 7.49, 7.16, 6.89, 6.79, 6.71, 6.62, 3.93, 2.97, 1.34 δ.

Preparation 100

Ethyl 5-(4-methylpiperazin-1-ylcarbonylamino) indole-2-carboxylate

Following the general procedure of EXAMPLE 20 and making non-critical variations but substituting methyl 5-aminoindole-2-carboxylate for 1-[5-aminoindole-2-carbonyl]-4-[3-(1-methylethylamino)-2-pyridinyl] piperazine, the title compound is obtained, NMR(CDCl$_3$) 7.62, 7.48, 7.22, 7.18, 7.08, 6.97, 6.75, 4.36, 3.49, 2.39, 2.28, 1.38 δ.

Preparation 101

5-(4-Methylpiperazin-1-ylcarbonylamino)indole-2-carboxylic acid

Following the general procedure of PREPARATION 84 and making non-critical variations but substituting ethyl 5-(4-methylpiperazin-1-ylcarbonylamino)indole-2-carboxylate (PREPARATION 100) for ethyl 5-[(3-(piperadin-1-yl)propyl)sulfonamido]indole-2-carboxylate, the title compound is obtained, NMR(CD$_3$OD) 7.70, 7.46, 7.32, 7.10, 7.05, 6.87, 3.54, 2.48, 2.32 δ.

Example 1

4-[2-(2-(2-Hydroxyethoxy)ethoxy)ethoxy] benzaldehyde (III)

4-Hydroxybenzaldehyde (II, 10.0 g) is dissolved in DMF (198 ml) and cooled to 0°, sodium hydride (60% in mineral oil, 3.44 g) is added, after bubbling ceased (15–20 min), 2-[2-(2-chloroethoxy)ethoxy]ethanol (17.8 ml) and sodium iodide (0.61 g) is added. The reaction is stirred at 20°–25° for 0.5 hours and heated to reflux for 78 hours. The reaction is poured into water and washed with ethyl acetate (3×). The phases are separated and the organic layer is washed with water, saline and concentrated under reduced pressure with heat. The material is purified with flash column chromatography, eluting with ethyl acetate/hexane (50/50) to (75/25). The appropriate fractions are pooled and concentrated to give the title compound, MS theory=254.1154, found=254.1163.

Example 2

Methyl 4-[(2-(2-hydroxyethoxy)ethoxy)ethoxy]-α-azidocinnamate (IV)

4-[2-(2-(2-Hydroxyethoxy)ethoxy)ethoxy]benzaldehyde (III, EXAMPLE 1, 17.3 g) and α-azidomethyl acetate (31.3 g) are dissolved in methanol (136 ml) and cooled to −10°. Sodium methoxide in methanol (25%, 77.7 ml) is added dropwise. The reaction is warmed to 20°–25° until TLC indicates the reaction is complete. The reaction mixture is poured into water and extracted with ethyl acetate. The phases are separated and the organic phase is concentrated and purified by flash column chromatography to give the title compound.

Example 3

Methyl 6-[(2-(2-hydroxyethoxy)ethoxy)ethoxy] indole-2-carboxylate (V)

Methyl 4-[(2-(2-hydroxyethoxy)ethoxy)ethoxy]-α-azidocinnamate (IV, EXAMPLE 2, 3.0 g) is dissolved in xylene (86 ml) and quickly heated to reflux. TLC indicates disappearance of starting material, the reaction is cooled to 20°–25° and the material is purified by flash column chromatography eluting with ethyl acetate/hexane (75/25). The appropriate fractions are pooled and concentrated to give the title compound, MS theory=323.1369, found=323.1366.

Example 4

6-[(2-(2-Hydroxyethoxy)ethoxy)ethoxy]indole-2-carboxylic acid (VI)

Methyl 6-[(2-(2-hydroxyethoxy)ethoxy)ethoxy]indole-2-carboxylate (V, EXAMPLE 3, 2.9 g) and potassium hydroxide (1.0 g) are dissolved in dioxane (25 ml) and water (5 ml). The reaction is warmed to 50° for 3 hours. The reaction is neutralized by the addition of hydrochloric acid (1N, 17 ml), extracted with THF/chloroform (50/50, 3×), washed with saline and concentrated under reduced pressure with heat. The material is purified by flash column chromatography eluting with methanol/chloroform/acetic acid (5/94/1). The appropriate fractions are pooled and concentrated to give the title compound, MS theory=309.1212, found=309.1208.

Example 5

1-[6-(2-(2-Hydroxyethoxy)ethoxy)ethoxyindolyl-2-carbonyl]-4-[3-(1-methylethylamino)-2-pyridinyl]piperazine (I)

6-[(2-(2-Hydroxyethoxy)ethoxy)ethoxy]indole-2-carboxylic acid (VI, EXAMPLE 4, 0.20 g) and 3-(1-methylethylamino)-2-pyridinyl]piperazine (0.157 g) is dissolved in THF (4 ml) and 1-(ethyl)-3-(dimethylaminopropyl)carbodiimide (0.16 g) is added. The reaction is stirred at 20°–24° for 2.75 hours, poured into chloroform, washed with saturated sodium bicarbonate and saline. The material is concentrated under reduced pressure with heat and purified by flash column chromatography eluting with methanol/chloroform (5/95). The appropriate fractions are pooled and concentrated to give the title compound, mp 157°–159°.

Example 6

1-[5-Nitroindolyl-2-carbonyl]-4-[3-(1-methylethylamino)-2-pyridinyl]piperazine 1-(Ethyl)-3-(dimethylaminopropyl)carbodiimide (0.45 g) is added to a solution of 1-[3-(1-methylethyl)amino)-2-pyridinyl]piperazine (PREPARATION 4, 0.43 g) and 5-nitroindole-2-carboxylic acid (0.86 g) in THF (5 ml). The reaction is stirred at 20°–25° for 3 hr, then it is dissolved in chloroform (50 ml) and extracted with saturated aqueous sodium bicarbonate, saline, dried over anhydrous sodium sulfate and concentrated under reduced pressure. Purification by flash column chromatography (200 g silica) eluting with ethyl acetate/hexane (50/50), the appropriate fractions are pooled and concentrated to give the title compound, mp 153°–154°.

Example 7

1-[5-Aminoindolyl-2-carbonyl]-4-[3-(1-methylethylamino)-2-pyridinyl]-piperazine (VII)

1-[5-Nitroindolyl-2-carbonyl]-4-[3-(1-methylethylamino)-2-pyridinyl]piperazine (EXAMPLE 6, 1.0 g) is dissolved in ethanol (60 ml) and THF (60 ml) and palladium on carbon (10%, 0.15 g) is added. The reaction is hydrogenated at 40 psi for 14 hr, then filtered through celite and concentrated under reduced pressure. Purification by flash chromatography, eluting with ethyl acetate/hexane (50/50→75/25), pooling and concentrating the appropriate fractions gives the title compound, mp 212°–214°.

Example 8

1-[5-Ethylenesulfonamidoindolyl-2-carbonyl]-4-[3-(1-methylethylamino)-2-pyridinyl]piperazine (IX)

1-[(5-Aminoindolyl-2-carbonyl]-4-[3-(1-methylethylamino)-2-pyridinyl]piperazine (V, EXAMPLE 7, 250 mg) is dissolved in pyridine (2 ml) and cooled to 0°. Then 2-chloroethane-sulfonyl chloride (VIII, 0.138 ml) is added dropwise. The reaction is warmed to 20°–25° and stirred for 3 hours. The reaction mixture is poured into aqueous saturated sodium bicarbonate and extracted with methylene chloride. The phases are separated and the organic layer is dried over anhydrous sodium sulfate and concentrated under reduced pressure with heat. Purification by flash column chromatography eluting with ethyl acetate/hexane (80/20). The appropriate fractions are pooled and concentrated to give the title compound, MS. m/e: 468, 453, 249, 219, 1922, 177 and 164.

Example 9

1-[5-(2-(1-Pyrrolidino)ethyl)sulfonamidoindolyl-2-carbonyl]-4-[3-(1-methylethylamino)-2-pyridinyl]piperazine (I)

1-[5-Ethylenesulfonamidoindolyl-2-carbonyl]-4-[3-(1-methylethylamino)-2-pyridinyl]-piperazine (IX, EXAMPLE 8, 173 mg), pyrrolidine (0.10 ml) and a catalytic amount of copper powder are refluxed together in xylene (5 ml) for 3.5 hours. The reaction is filtered through a pad of celite washing with ethyl acetate and methanol. After concentration under reduced pressure with heat, the product is purified by flash column chromatography eluting with methanol/chloroform (10/90). The appropriate fractions are pooled and concentrated to give the title compound which is crystallized from aqueous ethanol, mp 145°–146°.

Example 10

4-[2-(2-hydroxyethoxy)ethoxy]benzaldehyde (III)

Following the general procedure of EXAMPLE 1, and making non-critical variations but substituting 2-[2-chloroethoxy]ethanol for 2-[2-(2-chloroethoxy)ethoxy]ethanol, the title compound is obtained, NMR (CDCl$_3$) 7.82, 7.01, 4.21, 3.89, 3.76 and 3.66 δ.

Example 11

Methyl 4-[2-(2-hydroxyethoxy)ethoxy]-α-azidocinnamate (IV)

Following the general procedure of EXAMPLE 2, and making non-critical variations but substituting 4-[2-(2-hydroxyethoxy)ethoxy]benzaldehyde (III, EXAMPLE 10) for 4-[2-(2-(2-hydroxyethoxy)ethoxy)ethoxy]benzaldehyde (EXAMPLE I), the title compound is obtained, NMR (CDCl$_3$) 7.76, 6.92, 6.86, 4.15, 3.88, 3.86, 3.75 and 3.66 δ.

Example 12

Methyl 6-[(2-hydroxyethoxy)ethoxy]indole-2-carboxylate (V)

Following the general procedure of EXAMPLE 3, and making non-critical variations but substituting methyl 4-[2-

(2-hydroxyethoxy)ethoxy]-2-azidocinnamate (IV, EXAMPLE 11) for methyl 4-[(2-(2-hydroxyethoxy)ethoxy) ethoxy]-α-azidociannamate, the title compound is obtained, NMR (CDCl$_3$) 7.53, 7.14, 6.83, 4.14, 3.91, 3.87 and 3.68 δ.

Example 13

6-[(2-Hydroxyethoxy)ethoxy]indole-2-carboxylic acid (VI)

Following the general procedure of EXAMPLE 4, and making non-critical variations but substituting methyl 6-[ (2-hydroxyethoxy)ethoxy]indole-2-carboxylate (V, EXAMPLE 12) the title compound is obtained, NMR (d-methanol) 7.38, 6.95, 6.80, 6.63, 4.03, 3.74, 3.57, 3.51 and 3.17 δ.

Example 14

1-[6-(2-Hydroxyethoxy)ethoxyindolyl-2-carbonyl]-4-[3-(1-methylethylamino)-2-pyridinyl]piperazine (I)

Following the general procedure of EXAMPLE 5, and making non-critical variations but substituting 6-[(2-hydroxyethoxy)ethoxy]indole-2-carboxylic acid (VI, EXAMPLE 13) for 6-[(2-(2-hydroxyethoxy)ethoxy)ethoxy] indole-2-carboxylic acid, the title compound is obtained, mp 74°–75°.

Example 15

1-[5-(2-(1-Piperadinyl)ethyl)sulfonamidoindolyl-2-carbonyl]-4-[3-(1-methylethylamino)-2-pyridinyl] piperazine (I)

Following the general procedure of EXAMPLE 6, and making non-critical variations but substituting piperidine for pyrrolidine, the title compound is obtained, mp 150°.

Example 16

1-[5-(2-(1-Morpholinyl)ethyl)sulfonamidoindolyl-2-carbonyl]-4-[3-(1-methylethylamino)-2-pyridinyl] piperazine (I)

Following the general procedure of EXAMPLE 9, and making non-critical variations but substituting morpholine for pyrrolidine, the title compound is obtained, mp 135°.

Example 17

1-[6-(2-(2-Hydroxyethoxy)ethoxy)ethoxyindolyl-2-carbonyl]-4-[N-methyl-N-(3-(1-methylethylamino)-2-pyridinyl)amino]piperidine (I)

Following the general procedure of EXAMPLE 5, and making non-critical variations but substituting 4-(N-methyl-N-(3-(1-methylethylamino)-2-pyridinyl)amino)piperidine (PREPARATION 54) for 3-(1-methylethylamino)-2-pyridinyl]piperazine, the title compound is obtained, MS theory 540.3186, found 540.3149.

Example 18

1-[5-(3-Methylureido)-indolyl-2-carbonyl]-4-[N-methyl-N-(3-(1-methylethylamino)-2-pyridinyl) amino]-piperidine (I)

Methyl isocyanate (47 μl) is added to a solution of 1-[5-aminoindole-2-carbonyl]-4-[N-methyl-N-(3-(1-methylethylamino)-2-pyridinyl)amino]-piperidine (VII, PREPARATION 56, 310 mg) in dry methylene chloride (3 ml) of at 0°. The mixture is stirred for 30 min at 0°, during which a precipitate forms, and then at 20°–25° for 18 hrs. The reaction mixture is filtered and the precipitate rinsed with cold methylene chloride to give the title compound, NMR (methanol-d$_4$) 7.60, 7.32, 7.10, 6.98, 6.69, 4.46, 3.57, 3.37, 3.08, 2.75, 2.60, 1.82, 1.59 and 1.19 δ.

Example 19

1-[5-(2-(4-Pyridyl)-ethanesulfonamido)-indolyl-2-carbonyl]-4-[N-methyl-N-(3-(1-methylethylamino)-2-pyridinyl)amino]-piperidine (I)

A mixture of 4-pyridine ethanesulfonic acid (2.32 g), phosphorus pentachloride (2.86 g) and phosphorus oxychloride (9.4 ml) is heated to 60°, stirred for 1.5 hrs, cooled to 20°–25°, and diluted with carbon tetrachloride (10 ml). The mixture is filtered and the precipitate is washed thoroughly with carbon tetrachloride, acetonitrile, and ether and dried under reduced pressure to give the sulfonyl chloride as a solid. To a solution of 1-[5-aminoindolyl-2-carbonyl]-4-[N-methyl-N-(3-(1-methylethylamino)-2-pyridinyl)amino]-piperidine (VII, PREPARATION 56, 400 mg) in dry methylene chloride (5 ml) under nitrogen is added this sulfonyl chloride (262 mg) and triethylamine (275 μl). The mixture is stirred at 20°–25° for 24 hrs, during which an additional sulfonyl chloride (25 mg) and triethylamine (14 μl) are added, and then diluted with water (3 ml). The layers are separated and the organic phase is washed with saline (5 ml), dried over sodium sulfate, and concentrated under reduced pressure to give a solid which is chromatographed on silica gel (70–230 mesh, 45 g), 6leluting with a gradient of methanol/chloroform (2.5/97.5–7/93). Pooling of the appropriate fractions, having an R$_f$ of about 0.43 by TLC (methanol/chloroform, 10/90) and removal of solvent under reduced pressure gives the title compound, NMR (CDCl$_3$) 10.51, 8.62, 8.41, 7.71, 7.57, 7.35, 7.13, 6.98, 6.95, 6.85, 6.69, 4.62, 4.50, 3.55, 3.47, 3.40–2.90, 2.63, 1.92, 1.63 and 1.21 δ.

Example 20

1-[5-(4-Methylpiperazin-1-ylcarbonylamino)-indolyl-2-carbonyl]-4-[3-(1-methylethylamino)-2-pyridinyl)]piperazine (I)

Carbonyldiimidazole (0.086 g) is dissolved in dry THF (5 ml). 1-[5-Aminoindolyl-2-carbonyl]-4-[3-(1-methylethylamino)-2-pyridinyl]piperazine (VII, EXAMPLE 7, 0.19 g) is dissolved in dry THF (4 ml) and added to the carbonyldiimidazole solution over 2.4 hr. Upon the complete addition, N-methylpiperazine (55 μl) is added. The reaction mixture is allowed to stir overnight at 20°–25°. The reaction is then concentrated and the concentrate is dissolved in chloroform (15 ml) and washed with water and saline, dried over sodium sulfate, concentrated and dried under reduced pressure. The mixture is chromatographed over silica gel (20 ml) packed in chloroform eluting with 80 ml of chloroform, 100 ml each of 1% 1.5%, 2%, 2.5%, 3%, 4%, 5%, 6%, 7%, 8% and 10% and 150 ml of 15% methanol/chloroform. Fractions having an Rf value of about 0.28 in methanol/chloroform (10/90) are collected and concentrated to give a solid. The solid is recrystallized from methanol/chloroform, adding ethyl ether after crystals start to form to give the title compound, mp 200°.

Example 21

1-[6-Aminoindolyl-2-carbonyl]-4-[3-(1-methylethylamino)-2-pyridinyl]piperazine (VII)

Following the general procedure of EXAMPLE 7 and making non-critical variations but starting with 1-[6- nitroindolyl-2-carbonyl]-4-[3-(1-methylethylamino)-2-pyridinyl]piperazine (PREPARATION 64, 0.32 g), the title compound is obtained, mp 158° (decomp).

Example 28

1-[5-(2-(4-pyridyl)ethanesulfonamido)indole-2-carbonyl]-4-[3-(1-methylethylamino)-2-pyridinyl] piperazine (I)

Following the general procedure of EXAMPLE 19, and making non-critical variations but substituting 1-[5-aminoindole-2-carbonyl]-4-[3-(1-methylethylamino)-2-pyridinyl]piperazine (EXAMPLE 7) for 1-[5-aminoindole-2-carbonyl]-4-[N-methyl-N-(3-(1-methylethylamino)-2-pyridinyl)amino]piperidine, the title compound is obtained, NMR (CDCl$_3$) 10.67, 8.72, 8.41, 7.68, 7.56, 7.36, 7.13, 6.97, 6.92, 6.84, 6.72, 4.20, 4.07, 3.55, 3.28, 3.16, 3.08 and 1.25 δ.

Example 29

1-[5-(2-Dimethylaminoethanesulfonamido)indole-2-carbonyl]-4-[N-methyl-N-(3-(1-methylethylamino)-2-pyridinyl)amino]piperidine (I)

To a solution of 1-[5-aminoindole-2-carbonyl]-4-[N-methyl-N-(3-(1-methylethylamino)-2-pyridinyl)amino]piperidine (VII, PREPARATION 56, 400 mg) in dry methylene chloride (5 ml) under nitrogen at 0° is added triethylamine (275 µl) and 2-(dimethylamino)ethanesulfonyl chloride hydrochloride (225 mg). The mixture is stirred at 0° for 1 hr and at 20°–25° for 23 during which additional sulfonyl chloride (20 mg) and triethylamine (14 µl) are added. The mixture is then diluted with 4 ml of water, the layers are separated, and the organic phase is washed with saline, dried over sodium sulfate and concentrated under reduced pressure to give a solid which is chromatographed on silica gel (70–230 mesh, 46 g), eluting with a gradient of methanol/chloroform (2.5/97.5–6/94). Pooling of fractions having an R$_f$ of 0.36 by TLC (methanol/chloroform, 10/90) and removal of solvent under reduced pressure gives an impure solid. Purification of this solid on two 2000 µ preparative silica gel plates, eluting with methanol/chloroform (10/90) and extracting the appropriate band, gives the title compound, NMR (CDCl$_3$) 10.17, 7.71, 7.55, 7.35, 7.11, 6.94, 6.84, 6.69, 4.63, 4.50, 3.56, 3.45, 3.18, 3.30–3.00, 2.84, 2.63, 2.25, 1.93, 1.65 and 1.22 δ.

Example 30

1-[5-(2-Dimethylaminoethanesulfonamido)indole-2-carbonyl]-4-[3-(1-methylethylamino)-2-pyridinyl] piperazine (I)

Following the general procedure of EXAMPLE 29, and making non-critical variations but substituting 1-[5-aminoindole-2-carbonyl]-4-[3-(1-methylethylamino)-2-pyridinyl]piperazine (EXAMPLE 7, 400 mg) for 1-[5-aminoindole-2-carbonyl]-4-[N-methyl-N-(3-(1-methylethylamino)-2-pyridinyl)amino]piperidine, the title compound is obtained, mp 185°–188° (decomp).

Example 31

1-[5-(2-Phthalimidoethanesulfonamido)indole-2-carbonyl]-4-[N-methyl-N-(3-(1-methylethylamino)-2-pyridinyl)amino]piperidine (I)

To a solution of 1-[5-aminoindole-2-carbonyl]-4-[N-methyl-N-(3-(1-methylethylamino)-2-pyridinyl)amino] piperidine (PREPARATION 56, 606 mg) in dry methylene chloride (5 ml) under nitrogen is added pyridine (127 µl, 1.05 equivalents) and 2-phthalimidoethanesulfonyl chloride (400 mg). The mixture is stirred at 20°–25° for 3 days and then diluted with methylene chloride (40 ml) and water (20 ml). The layers are separated and the organic phase is washed with saline (15 ml), dried over sodium sulfate, and concentrated under reduced pressure to give a residue which is then chromatographed on silica gel (230–400 mesh, 85 g, 8 psi), eluting with a gradient of methanol/chloroform (1/99–2.5/97.5). The appropriate fractions (R$_f$=0.33, TLC, methanol/chloroform, 5/95) are pooled and concentrated to give the title compound, NMR (CDCl$_3$) 10.33, 7.80, 7.76–7.63, 7.35, 7.22, 6.95, 6.85, 6.69, 4.65, 4.51, 4.13, 3.60–3.40, 3.40–2.90, 2.64, 1.94, 1.65 and 1.22 δ.

Example 32

1-[5-(2-Aminoethanesulfonamido)indole-2-carbonyl]-4-[N-methyl-N-(3-(1-methylethylamino)-2-pyridinyl)amino]piperidine (I)

To a solution of 1-[5-(2-phthalimidoethanesulfonamido) indole-2-carbonyl]-4-[N-methyl-N-(3-(1-methylethylamino)-2-pyridinyl)amino]piperidine (EXAMPLE 31, 675 mg) in 95% ethanol (10 ml) under nitrogen is added hydrazine monohydrate (53 µl). The mixture is stirred at 70°–75° for 20 hrs during which additional hydrazine monohydrate (10 µl) is added, concentrated to remove ethanol, diluted with water (10 ml), acidified to pH 2 with 1M hydrochloric acid and stirred for 10 min. The mixture is then filtered, the filtrate is adjusted to pH 10–11, and the resulting precipitate is isolated by filtration to give the title compound, NMR (CDCl$_3$) 9.86, 7.70, 7.56, 7.29, 7.10, 6.94, 6.84, 6.68, 4.60, 4.50, 3.56, 3.44, 3.40–2.80, 2.62, 1.93, 1.65 and 1.22 δ. The basic filtrate is extracted with methylene chloride (2×15 ml) which is then washed with saline (10 ml), dried over sodium sulfate, and concentrated under reduced pressure to give an additional amount of the title compound.

Example 33

1-[5-(2-Phthalimidoethanesulfonamido)indole-2-carbonyl]-4-[3-(1-methhylethylamino)-2-pyridinyl] piperazine (I)

Following the general procedure of EXAMPLE 31, and making non-critical variations but substituting 1-[5-aminoindole-2-carbonyl]-4-[3-(1-methhylethylamino)-2-pyridinyl]piperazine (EXAMPLE 7, 553 mg) for 1-[5-aminoindole-2-carbonyl]-4-[N-methyl-N-(3-(1-methhylethylamino)-2-pyridinyl)amino]piperidine and using 2 equivalents of pyridine instead of 1.05 equivalents, the title compound is obtained, NMR (CDCl$_3$) 10.30, 7.78, 7.66, 7.36, 7.23, 6.95, 6.86, 6.73, 4.25–4.02, 3.57, 3.44, 3.18 and 1.26 δ.

Example 34

1-[5-(2-Aminoethanesulfonamido)indole-2-carbonyl]-4-[3-(1-methylethylamino)-2-pyridinyl] piperazine (I)

Following the general procedure of EXAMPLE 32, and making non-critical variations but substituting 1-[5-(2-phthalimidoethanesulfonamido)indole-2-carbonyl]-4-[3-(1-methhylethylamino)-2-pyridinyl]piperazine (EXAMPLE 33, 605 mg) for 1-[5-(2-(phthalimidoethanesulfonamido)

indole-2-carbonyl]-4-[N-methyl-N-(3-(1-methylethylamino)-2-pyridinyl)amino]piperidine, the title compound is obtained, NMR (CDCl₃) 10.62, 7.68, 7.55, 7.25, 7.07, 6.93, 6.84, 6.69, 4.20, 4.04, 3.90–3.50, 3.14 and 1.25 δ.

Example 35

1-[5-(4-Methyl-1-piperazinosulfonylamino)indole-2-carbonyl]-4-[N-methyl-N-(3-(1-methylethylamino)-2-pyridinyl)amino]piperidine (I)

To a solution of 1-methylpiperazine (1.11 ml) in dry methylene chloride (20 ml) at 0° under argon is added sulfuryl chloride (1.6 ml) dropwise. The mixture is warmed to 20°–25°, stirred for 1.5 hrs, and concentrated to give the crude sulfamoyl chloride intermediate. This intermediate (187 mg) is added to a solution of 1-[5-aminoindole-2-carbonyl]-4-[N-methyl-N-(3-(1-methylethylamino)-2-pyridinyl)amino]-piperidine (PREPARATION 56, 162 mg) in pyridine (1.5 ml) under nitrogen, and the resulting mixture is stirred at 20°–25° for 20 hrs, diluted with water (25 ml), and extracted with methylene chloride (4×25 ml). The organic phase is then washed with aqueous sodium bicarbonate solution (30 ml) and saline (50 ml), dried over sodium sulfate, and concentrated under reduced pressure to give a solid which is chromatographed on four 2000 μ preparative silica gel plates, eluting with methanol/chloroform (5/95) twice. Extraction of the extract of the appropriate band gives the title compound, NMR (CDCl₃) 9.94, 7.71, 7.54, 7.30, 7.13, 6.95, 6.84, 6.69, 4.64, 4.50, 3.56, 3.45, 3.25, 2.63, 2.36, 2.23, 1.95, 1.65 and 1.22 δ.

Example 36

1-[5-(Dimethylaminosulfonylamino)indole-2-carbonyl]-4-[N-methyl-N-(3-(1-methylethylamino)-2-pyridinyl)amino]piperidine (I)

To a solution of 1-[5-aminoindole-2-carbonyl]-4-[N-methyl-N-(3-(1-methylethylamino)-2-pyridinyl)amino] piperidine (PREPARATION 56, 91 mg) in pyridine (0.5 ml) under nitrogen is added N,N-dimethylsulfamoyl chloride. The mixture is stirred at 20°–25° for 16 hr and then diluted with methylene chloride (35 ml) and 1M hydrochloric acid (20 ml). The layers are separated and the organic layer is washed with 1M hydrochloric acid (20 ml) and saline, dried over sodium sulfate, and concentrated to give a solid film which is then chromatographed on two 2000 μ preparative silica gel plates, eluting with methanol/chloroform (5/95). The desired band is extracted and concentrated to give the title compound, NMR (CDCl₃) 10.34, 7.72, 7.64, 7.56, 7.37, 7.16, 6.95, 6.84, 6.70, 4.65, 4.50, 3.56, 3.46, 3.40–3.00, 2.80, 2.63, 1.93, 1.64 and 1.22 δ.

Example 37

1-[5-(4-Methyl-1-piperazinosulfonylamino)indole-2-carbonyl]-4-[3-(1-methylethylamino)-2-pyridinyl]piperazine (I)

To a solution of 1-methylpiperazine (1.11 ml) in dry methylene chloride (10 ml) at 0° under argon is added freshly distilled sulfuryl chloride (1.60 ml) dropwise. The mixture is warmed to 20°–25° and stirred for 2.25 hrs, after which a dark brown gum is removed from the mixture. The remaining reaction mixture is concentrated under reduced pressure to give the sulfamoyl chloride intermediate (NMR (pyridine-d₅) 3.56, 2.77 and 2.40 δ). This intermediate (115 mg) is added to a solution of 1-[5-aminoindole-2-carbonyl]-4-[3-(1-methylethylamino)2-pyridinyl]piperazine (EXAMPLE 7, 200 mg) and pyridine (94 μl) in dry methylene chloride (3 ml) under nitrogen. The mixture is stirred at 20°–25° for 6 days during which an additional mount of the sulfamoyl chloride (50 mg) and pyridine (40 μl) is added, concentrated under reduced pressure, and diluted with methylene chloride (30 ml) and water (10 ml). The layers are separated, the aqueous phase is extracted with methylene chloride (2×25 ml), and the combined organic layers are washed with saline (20 ml), dried over sodium sulfate, and concentrated under reduced pressure. The resulting solid is chromatographed on silica gel (230–400 mesh, 35 g, 5 psi), eluting with a gradient of methanol/chloroform (4/96–7/93). Pooling of the appropriate fractions (R_f=0.25, TLC, methanol/chloroform, 10/90) and concentrating gives the title compound, NMR (CDCl₃) 10.45, 8.00, 7.70, 7.55, 7.29, 7.12, 6.93, 6.85, 6.72, 4.21, 4.10, 3.57, 3.23, 3.18, 2.36, 2.22 and 1.26.

Example 38

1-[5-(4-Benzyl-1-piperazinnosulfonylamino)indole-2-carbonyl]-4-[3-(1-methylethylamino)-2-pyridinyl]piperazine (I)

Following the general procedure of EXAMPLE 37, and making non-critical variations but substituting 1-benzylpiperazine for 1-methylpiperazine, the title compound is obtained, mp 173°–176°.

Example 39

1-[5-(1-piperazinosulfonylamino)indole-2-carbonyl]-4-[3-(1-methylethylamino)-2-pyridinyl]piperazine (I)

Palladium on carbon (10%, 300 mg) is added to a solution of 1-[5-(4-benzylpiperazinosulfonylamino)indole-2-carbonyl]-4-[3-(1-methylethylamino)-2-pyridinyl] piperazine (EXAMPLE 38, 450 mg) in methanol (50 ml). The mixture is stirred under a hydrogen atmosphere (balloon) for 4.5 hrs, under nitrogen for 17 hrs, again under hydrogen for 8 hrs and nitrogen for 17 hrs, and then under hydrogen for an additional 3 hrs. The mixture is filtered through a pad of celite and the filtrate concentrated under reduced pressure to give a solid film which is then chromatographed on silica gel (230–400 mesh, 37 g, 5–6 psi), eluting with a gradient of methanol/chloroform (5/95–10/90). Pooling of the appropriate fractions (R_f=0.18, TLC, methanol/chloroform, 10/90) and concentrating gives the title compound, NMR (methanol-d₄) 7.56, 7.39, 7.18, 6.98, 6.82, 4.02, 3.63, 3.16, 3.09, 2.71 and 1.24.

Example 40

1-[5-(Morpholinosulfonylamino)indole-2-carbonyl]-4-[3-(1-methylethylamino)-2-pyridinyl]piperazine (I)

Following the general procedure of EXAMPLE 37, and making non-critical variations but substituting morpholine (543 μl) for 1-methylpiperazine, the crude product is obtained. This residue is chromatographed on silica gel (230–400 mesh, 100 g, 6–8 psi), eluting with a gradient of ethyl acetate/hexane (35/65–100/0). Pooling of the appropriate fractions (R_f=0.16, TLC, ethyl acetate/hexane, 2×50/50), concentrating under reduced pressure, and triturating with methanol gives the title compound, mp 210°–211.5°.

Example 41

1-[5-Aminoindole-2-carbonyl]-4-[3-(1,1-dimethylpropylamino)-2-pyridinyl]piperazine To a solution of 1-[5-nitroindole-2-carbonyl]-4-[3-(1,1-dimethylpropylamino)-2-pyridinyl]piperazine (PREPARATION 67, 1.00 g) in dimethylformamide/methanol (200 ml, 50/50) under nitrogen is added palladium on carbon (10%, 250 mg). The mixture is put under hydrogen (balloon) for 4 hr and nitrogen for 17 hr, filtered through a pad of celite, and concentrated under reduced pressure to give the title compound, NMR (CDCl$_3$) 9.25, 7.66, 7.24, 7.06, 6.88, 6.76, 6.63, 4.58, 4.05, 3.35, 3.14, 1.73, 1.35 and 0.91.

Example 42

1-[5-(4-Methylpiperazinosulfonylamino)indole-2-carbonyl]-4-[3-(1,1-dimethylpropylamino)-2-pyridinyl]piperazine (I)

Following the general procedure of EXAMPLE 37, and making non-critical variations but substituting 1-[5-aminoindole-2-carbonyl]-4-[3-(1,1-dimethylpropylamino)-2-pyridinyl]-piperazine (EXAMPLE 41) for 1-[5-aminoindole-2-carbonyl]-4-[3-(1-methylethylamino)-2-pyridinyl]piperazine, the title compound is obtained, mp 202°–205° (decomp).

Example 43

1-[5-(Methanesulfonamido)indole-2-carbonyl]-4-[3-(1,1-dimethylpropylamino)-2-pyridinyl]piperazine To a solution of 1-[5-aminoindole-2-carbonyl]-4-[3-(1,1-dimethylpropylamino)-2-pyridinyl]piperazine (EXAMPLE 41, 300 mg) in dry methylene chloride (6 ml) under nitrogen is added pyridine (119 µl) and methanesulfonyl chloride (57 µl). The mixture is stirred at 20°–25° for 24 hr and then diluted with methylene chloride (20 ml) and water (8 ml). The layers are separated and the organic phase is washed with saline (8 ml), dried over sodium sulfate, and concentrated to give a solid which is then chromatographed on silica gel (230–400 mesh, 34 g, 5–6 psi), eluting with methanol/chloroform (2.5/97.5). Pooling of the appropriate fractions, concentration to a solid, and recrystallization from chloroform gives the title compound, mp 232°–233° (decomp).

Example 44

1-[5-(4-(1,1-Dimethylpropyl)piperazinosulfonylamino)indole-2-carbonyl]-4-[3-(1-methylethylamino)-2-pyridinyl]piperazine (I)

Following the general procedure of EXAMPLE 40, and making non-critical variations but substituting 1-(1,1-dimethylpropyl)piperazine (PREPARATION 70) for 1-methylpiperazine and working up the reaction after 2 days, the title compound is obtained, mp 158°–160°.

Example 45

1-[5-Methanesulfonamidoindole-2-carbonyl]-4-[N-methyl-N-(3-(1,1-dimethylpropylamino) -2-pyridinyl)amino]piperidine Following the general procedure of EXAMPLE 43, but substituting 1-[5-aminoindole-2-carbonyl]-4-[N-methyl-N-(3-(1,1-dimethylpropylamino)-2-pyridinyl)amino]piperidine (PREPARATION 75) for 1-[5-aminoindole-2-carbonyl]-4-[3-(1,1-dimethylpropylamino)-2-pyridinyl]piperazine and eliminating the re, crystallization, the title compound is obtained, NMR (CDCl$_3$) 10.06, 7.70, 7.58, 7.39, 7.16, 7.08, 6.91, 6.71, 4.90, 4.63, 3.45, 3.20, 2.95, 2.64, 1.94, 1.68, 1.32 and 0.87 δ.

Example 46

1-[5-(1-piperazinylcarbonylamino)-indole-2-carbonyl]-4-[3-(1-methylethylamino)-2-pyridinyl]piperazine (I)

Following the general procedure of EXAMPLE 20 and making non-critical but substituting piperazine for N-methylpiperazine, the title compound is obtained, mp 209° (decomp).

Example 47

1-[5-(N-phenyl-N-methyluriedo)-indole-2-carbonyl]-4-[3-(1-methylethylamino)-2-pyridinyl]piperazine (I)

Following the general procedure of EXAMPLE 20 and making non-critical variations but substituting N-methylaniline for N-methylpiperazine, the title compound is obtained, NMR (chloroform-d) 9.45, 7.71, 7.39, 6.95, 6.71, 6.25, 4.19, 4.05, 3.62, 3.36, 3.17, 1.26 δ.

Example 48

1-[5-(N-(2-dimethylaminoethyl)-N-methyluriedo)-indole-2-carbonyl]-4-[3-(1-methylethylamino)-2-pyridinyl]piperazine (I)

Following the general procedure of EXAMPLE 20 and making non-critical variations such as the addition of N-methyl-2-pyrrolidinone as a cosolvent, and substituting N,N,N'-trimethylethylenediamine for N-methylpiperazine, the title compound is obtained, NMR (chloroform-d) 10.1, 9.42, 7.68, 7.31, 7.10, 7.09, 6.95, 6.85, 6.72, 4.20, 4.07, 3.58, 3.39, 3.18, 3.0, 2.60, 2.41, 1.26 δ.

Example 49

1-[5-(N-(2-dimethylaminoethyl)uriedo)-indole-2-carbonyl]-4-[3-(1-methylethylamino)-2-pyridinyl]piperazine (I)

Following the general procedure of EXAMPLE 48 and making non-critical variations but substituting N,N-dimethylethylenediamine for N,N,N'-trimethylethylenediamine, the title compound is obtained, mp 124° (decomposition).

Example 50

1-[5-(N-(2-methylaminoethyl)-N-methyluriedo)-indole-2-carbonyl]-4-[3-(1-methylethylamino)-2-pyridinyl]piperazine (I)

Following the general procedure of EXAMPLE 48 and making non-critical variations but substituting N,N'-dimethylethylenediamine for N,N,N'-trimethylethylenediamine, the title compound is obtained, mp 197° (decomposition).

Example 51

1-[5-(N-(3-pyridyl)uriedo)-indole-2-carbonyl]-4-[3-(1-methylethylamino)-2-pyridinyl]piperazine (I)

Following the general procedure of EXAMPLE 20 and making non-critical variations but substituting 3-aminopyridine for N-methylpiperazine, the title compound is obtained, NMR (chloroform-d) 11.52, 8.79, 8.64, 8.17, 7.98, 7.58, 7.32, 7.20, 6.95, 6.81, 4.50, 3.96, 3.62, 3.03, 1.19 δ.

Example 52

1-[5-((3,5-cis-dimethyl-1-piperazinyl)carbonylamino)-indole-2-carbonyl]-4-[3-(1-methylethylamino)-2-pyridinyl]piperazine (I)

Following the general procedure of EXAMPLE 20 and making non-critical variations such as including N-methyl-2-pyrrolidinone as a cosolvent and substituting cis-2,6-dimethylpiperazine for N-methylpiperazine, the title compound is obtained, mp 157° (decomposition).

Example 53

1-[5-((3,5-cis-dimethyl-1-piperazinyl)carbonylamino)-indole-2-carbonyl]-4-[3-(1,1-dimethylethylamino)-2-pyridinyl]piperazine (I)

Following the general procedure of EXAMPLE 20 but substituting cis-3,5-dimethylpiperazine for N-methylpiperazine and substituting 1-[5-aminoindole-2-carbonyl]-4-[3-(1,1-dimethylethylamino)-2-pyridinyl]piperazine (PREPARATION 99) for 1-[5-aminoindole-2-carbonyl]-4-[3-(1-methylethylamino)-2-pyridinyl]piperazine the title compound is obtained, mp 162° (decomposition).

Example 54

1-[5-((4-methyl-1-piperazine-4-oxide)ylcarbonylamino)-indole-2-carbonyl]-4-[3-(1-methylethylamino)-2-pyridinyl]piperazine (I)

To a solution of 1-[5-(4-methyl-1-piperazinylcarbonylamino)-indole-2-carbonyl]-4-[3-(1-methylethylamino)-2-pyridinyl]piperazine (EXAMPLE 20, 0.1 g) in methanol (8.0 ml) is added hydrogen peroxide (3.11%, 0.22 ml). Additional hydrogen peroxide was added in portions over 3 hr (total of 1.16 ml) until total conversion of the substrate is achieved as indicated by TLC on silica gel (methanol). The mixture is concentrated, dissolved in methylene chloride, dried over sodium sulfate and concentrated to yield the title compound, NMR (chloroform-d) 7.60, 7.56, 7.38, 7.20, 6.98, 4.03, 3.67, 3.46, 3.20, 3.08, 1.24 δ.

Example 55

1-[5-(4-(1-methylethyl)-1-piperazinylcarbonylamino)-indole-2-carbonyl]-4-[3-(1-methylethylamino)-2-pyridinyl]piperazine (I)

To a solution of 1-[5-(1-piperazinylcarbonylamino)-indole-2-carbonyl]-4-[3-(1-methylethylamino)-2-pyridinyl]piperazine (EXAMPLE 46, 0.41 g) in methanol (50 ml) is added sodium cyanoborohydride (53 mg) and acetone (1 ml). Additional sodium cyanoborohydride (44.3 mg total) and excess acetone are added in portions until the reaction is complete as judged by TLC on silica gel. The mixture is acidified with acetic acid, neutralized with 50% aqueous sodium hydroxide and concentrated. The residue is dissolved in methylene chloride, washed with water, saturated potassium carbonate solution, and saline and dried over sodium sulfate followed by concentration. The resulting material is purified by chromatography on silica gel (100 ml) packed in methanol/chloroform (1/99) and eluted with a methanol/chloroform gradient (1→5%) to give the title compound, NMR (chloroform-d) 9.14, 7.71, 7.33, 7.17, 6.95, 6.86, 6.74, 4.06, 3.58, 3.20, 2.78, 2.60, 1.27, 1.08 δ.

Example 56

1-[5-(cis-3,4,5-trimethyl-1-piperazinylcarbonylamino)-indole-2-carbonyl]-4-[3-(1-methylethylamino)-2-pyridinyl]piperazine (I)

Following the general procedure of EXAMPLE 20 and making non-critical variations but substituting cis-3,4,5-trimethylpiperazine (PREPARATION 77) for N-methylpiperazine, the title compound is obtained, NMR (chloroform-d) 7.91, 7.57, 7.36, 7.18, 7.01, 6.81, 4.02, 3.63, 3.10, 2.72, 2.33, 2.26, 1.25, 1.16 δ.

Example 57

1-[5-(4-methyl-1-piperazinylcarbonylamino)-indole-2-carbonyl]-4-[3-(1-methylethylamino)-2-pyridinyl]piperazine (I)

Carbonyldiimidazole (1.54 g) is dissolved in of dry THF (40 ml). 1-[5-aminoindole-2-carbonyl]-4-[3-(1-methylethylamino)-2-pyridinylpiperazine (VII, EXAMPLE 7, 3.0 g) and N-methylpiperazine (1.3 ml) are dissolved in dry THF (75 ml) and added to the carbonyldiimidazole solution over 1.5 hr. After an additional hour the reaction is concentrated and the concentrate is dissolved in methylene chloride (125 ml) and washed with water and saline, dried over sodium sulfate, concentrated and dried under reduced pressure. The mixture is chromatographed over silica gel (450 ml) packed in 2% methanol/methylene chloride eluting with a methanol/methylene chloride gradient (2→50%). Fractions with an $R_f$ value of about 0.14 in methanol/chloroform (10/90) are collected and concentrated to give a solid. The solid is dissolved in chloroform (100 ml/1 g of solid), filtered and the solution is concentrated to dryness to afford the title compound. The solid is recrystallized from methanol/chloroform, adding ethyl ether as crystals begin to form to give the title compound, mp 200°.

Example 58

1-[5-(4-(1,1-dimethylpropyl)-1-piperazinylcarbonylamino)-indole-2-carbonyl]-4-[3-(1-methylethylamino)-2-pyridinyl]piperazine (I)

Following the general procedure for EXAMPLE 57 and making non-critical variations but substituting N-(1,1-dimethylpropyl)piperazine (PREPARATION 70) for N-methylpiperazine, the title compound is obtained, Mp 240°–242°.

Example 59

1-[5-(4-morpholinocarbonylamino)-indole-2-carbonyl]-4-[3-(1-methylethylamino)-2-pyridinyl]piperazine (I)

Following the general procedure for EXAMPLE 57 and making non-critical variations but substituting morpholine for N-methylpiperazine, the title compound is obtained, mp 133°–136°.

Example 60

1-[5-(4-Methyl-1-piperazinylcarbonylamino)indole-2-carbonyl]-4-[3-(1,1-dimethylpropylamino)-2-pyridinyl]piperazine (I)

Following the general procedure for EXAMPLE 57 and making non-critical variations but substituting 1-[5- aminoindole-2-carbonyl]-4-[3-(1,1-dimethylpropylamino)-2-pyridinyl]piperazine (EXAMPLE 41) for 1-[5-aminoindole-2-carbonyl]-4-[3-(1-methylethylamino)-2-pyridinylpiperazine the title compound is obtained, NMR (chloroform-d) 10.02, 7.68, 7.62, 7.21, 7.07, 6.97, 6.88, 6.61, 4.90, 4.59, 3.50, 3.38, 3.11, 2.61, 2.36, 2.23, 1.90, 1.64, 1.31, 0.86 δ.

Example 61

1-[6-[2-(2-Methoxyethoxy)ethoxyindolyl-2-carbonyl]-4-[3-(1-methylethylamino)-2-pyridinyl]piperazine (I)

6-[2-(2-Methoxyethoxy)ethoxy]indole-2-carboxylic acid (VI, PREPARATION 81, 0.30 g) and 3-(1-methylethylamino)-2-pyridinyl]piperazine (0.26 g) is dissolved in THF (5.35 ml) and 1-(ethyl-3-(dimethylaminopropyl)carbodiimide (EDC, 0.25 g) is added. The reaction is stirred 2.75 hr at 20°–25° and poured into chloroform, washed with saturated sodium bicarbonate and saline. The material is concentrated under reduced pressure and purified by flash column chromatography eluting with methanol/chloroform (2.5/97.5). The appropriate fractions are pooled and concentrated to provide the title compound, mp 135°–136°.

Example 62

1-[6-(2-(1-Piperadinyl)ethoxy)indolyl-2-carbonyl]-4-[3-(1-methylethylamino)-2-pyridinyl]piperazine Following the general procedure of EXAMPLE 5, and making non-critical variations but substituting 6-[(2-piperadin-1-yl)ethoxy]indole-2-carboxylic acid (PREPARATION 94) for 6-[(2-(2-hydroxyethoxy)ethoxy]indole-2-carboxylic acid, the title compound is obtained, mp 139°–141°.

Example 63

1-[5-(3-(1-Piperadinyl)propyl)sulfonamidoindolyl-2-carbonyl]-4-[3-(1-methylethylamino)-2-pyridinyl]piperazine (I)

1-[5-(3-Chloropropyl)sulfonamidoindolyl-2-carbonyl]-4-[3-(1-methylethylamino)-2-pyridinyl]piperazine (PREPARATION 86, 0.60 g), piperadine (0.115 ml) and sodium iodide (0.174 g) are placed in 5.8 ml of acetonitrile and refluxed for 28 hr. Then the reaction is diluted with chloroform, washed with water, saline, dried over anhydrous sodium sulfate and concentrated under reduced pressure. Purification by flash column chromatography eluting with methanol/chloroform (2.5/97.5), pooling and concentrating the appropriate fractions gives the title compound, mp 145°–146°.

Example 64

1-[5-(3-(1-Piperadinyl)propyl)sulfonamidoindolyl-2-carbonyl]-4-[3-(1,1-dimethylethylamino)-2-pyridinyl]piperazine (I)

Following the general procedure of EXAMPLE 5, and making non-critical variations but substituting 5-[(3-(1-piperadinyl)propyl)sulfonamido]indole-2-carboxylic acid (PREPARATION 84) for 6-[(2-(2-hydroxyethoxy)ethoxy]indole-2-carboxylic acid, the title compound is obtained, mp 118°–120°.

Example 65

1-[5-(3-(Morpholinyl-1-yl)propyl)sulfonamidoindolyl-2-carbonyl]-4-[3-(1,1-dimethylethylamino)-2-pyridinyl]piperazine (I)

1-[5-Aminoindolyl-2-carbonyl]-4-[3-(1-methylethylamino)-2-pyridinyl]-piperazine (EXAMPLE 7, 0.50 g) and 0.37 ml of triethylamine are dissolved in 2.6 ml of methylene chloride and cooled to 20°–25°. Then 0.35 g of 3-(morpholin-1-ylpropyl)sulfonyl chloride hydrochloride (prepared by dissolving 5.0 g of 4-morpholinepropanesulfonic acid in 10 ml of phosphorus oxychloride and adding 4.97 g of phosphorus pentachloride and stirring overnight at 20°–25°. Then concentrating under reduced pressure, chasing with benzene, collecting the solids and washing with carbon tetrachloride and ether) is added and the reaction is slowly allowed to warm to 20°–25° and stirred for 4 hr. Then the reaction is diluted with chloroform, washed with saturated aqueous sodium bicarbonate, dried over anhydrous sodium sulfate and concentrated under reduced pressure. Purification by flash column chromatography eluting with methanol/chloroform (3/97), pooling and concentrating the appropriate fractions and crystallizing from ethyl acetate gives the title compound, mp 183°–185°.

Example 66

1-[5-Methoxy-6-(2-(1-morpholinyl)ethoxy)indolyl-2-carbonyl]-4-[3-(1-methylethylamino)-2-pyridinyl]piperazine Following the general procedure of EXAMPLE 5, and making non-critical variations but substituting 5-methoxy-6-[2-(1-morpholinyl)ethoxy]indole-2-carboxylic acid (PREPARATION 90) for 6-[(2-(2-hydroxyethoxy)ethoxy]indole-2-carboxylic acid, the title compound is obtained, mp 229°–231°.

Example 67

1-[5-((4-Methylpiperazin-1-yl)thiocarbonylamino)indolyl-2-carbonyl]-4-[3-(1-methylethylamino)-2-pyridinyl]piperazine (I)

1-[5-Aminoindolyl-2-carbonyl]-4-[3-(1-methylethylamino)-2-pyridinyl]-piperazine (PREPARATION 71, 0.20 g) is dissolved in 1.4 ml of THF and is added dropwise to a 0° solution of 0.105 g of thiocarbonyldiimidazole in 1.4 ml of THF. The reaction is stirred 45 min and then methylpiperazine (0.06 ml) is added and the reaction is stirred a further 30 min at 0°. Then the reaction is diluted with chloroform, washed with saturated aqueous sodium bicarbonate, dried over anhydrous sodium sulfate and concentrated under reduced pressure. Purification by flash column chromatography eluting with chloroform/methanol (9/1), pooling and concentrating the appropriate fractions gives the title compound, mp 218°–220°.

Example 68

1-[5-(3-(3-Morpholin-1-ylpropyl)thioureido)indolyl-2-carbonyl]-4-[3-(1-methylethylamino)-2-pyridinyl]piperazine (I)

1-[5-Aminoindolyl-2-carbonyl]-4-[3-(1-methylethylamino)-2-pyridinyl]-piperazine (EXAMPLE 7, 0.5 g) is dissolved in 2.6 ml of THF and cooled to 0°. Then 3-morpholinopropylisothiocyanate (0.25 ml) is added and the reaction is slowly warmed to 20°–25° and stirred for 18 hr. Then the reaction is diluted with chloroform, washed with saturated aqueous sodium bicarbonate, dried over anhydrous sodium sulfate and concentrated. Crystallization from ethyl acetate/hexane provided the title compound, mp 187°–189°.

Example 69

1-[5-Dimethylaminosulfamoylaminoindolyl-2-carbonyl]-4-[3-(1-methylethylamino)-2-pyridinyl]piperazine (I)

1-[5-Aminoindolyl-2-carbonyl]-4-[3-(1-methylethylamino)-2-pyridinyl]-piperazine (EXAMPLE 7, 0.485 g) is dissolved in 3 ml of acetonitrile and 0.10 ml of pyridine is added. The reaction is cooled to 0° and the dimethylaminosulfamoylchloride (0.14 ml) is added in one portion. The reaction is warmed to 20°–25° and stirred for 48 hr. Then it is poured into saturated aqueous sodium bicarbonate and extracted with methylene chloride, dried over anhydrous sodium sulfate and concentrated under reduced pressure. Purification by flash column chromatography eluting with a gradient of 50% ethyl acetate/hexane to 100% ethyl acetate), pooling and concentrating the appropriate fractions gives the title compound, mp 174°–175°.

Example 70

1-[5-(Piperadin-4-yl)amido)indolyl-2-carbonyl]-4-[3-(1-methylethylamino)-2-pyridinyl]piperazine 1-[5-((1-Carbobenzyloxy)piperadin-4-yl)amido)indolyl-2-carbonyl]-4-[3-(1-methylethylamino)-2-pyridinyl]piperazine (PREPARATION 85, 0.30 g) is dissolved in 20 ml of ethanol and 0.10 g of 10% palladium on carbon is added. The reaction is placed on a Parr hydrogenator under 40 psi of hydrogen for 4 hr. The reaction is filtered through celite, concentrated under reduced pressure and crystallized from ethyl acetate/hexane/methanol to provide the title compound, mp(dec) 172°–178°.

Example 71

1-[5-((1-(1-Methylethylpiperadin-4-yl)amido)indolyl-2-carbonyl]-4-[3-(1-methylethylamino)-2-pyridinyl]piperazine 1-[5-(Piperadin-4-yl)amido)indolyl-2-carbonyl]-4-[3-(1-methylethylamino)-2-pyridinyl]piperazine (EXAMPLE 70, 0.40 g) and acetone (0.066 ml) are dissolved in 1.6 ml of methanol and sodium cyanoborohydride (0.054 g) is added. After 1 hr of stirring at 20°–25°, 10–15 mg of sodium cyanoborohydride and 10–15 ml of acetone are added every hour for 7 hr. Then the reaction is stirred overnight at 20°–25°. It is diluted with chloroform, washed with saturated sodium bicarbonate, saline, dried over anhydrous sodium sulfate and concentrated under reduced pressure. Crystallization from ethyl acetate afforded the title compound, mp 217°–219°.

Example 72

1-[5-Trifluoroacetamidoindolyl-2-carbonyl]-4-[3-(1-methylethylamino)-2-pyridyl]

1-[5-Aminoindolyl-2-carbonyl]-4-[3-(1-methylethylamino)-2-pyridyl]piperazine (EXAMPLE 7, 0.30 g, 0.79 mmol) is dissolved in 1.6 ml of methylene chloride and pyridine (0.064 ml, 0.79 mmol) is added. The reaction was cooled to 0° and trifluoroacetic anhydride (0.11 ml, 0.79 mmol) is added dropwise. The reaction is stirred for 2 hr at 0° and then an additional 0.2 equivalents of trifluoroacetic anhydride is added and the reaction was stored at 0° for 18 hr. The mixture is diluted with chloroform, washed with water, saline, dried over anhydrous sodium sulfate and concentrated under reduced pressure. Purification by flash column chromatography, eluting with methanol/chloroform (2/98), pooling and concentration of the appropriate fractions gives the title compound, mp 215°–218°; NMR(300 MHz, CD$_3$OD) 7.88, 7.81, 7.47, 7.36, 7.30, 6.90, 6.78, 3.95, 3.54, 3.01, 1.16 δ.

Example 73

1-[5-Methoxycarbamoylindolyl-2-carbonyl]-4-[3-(1-methylethylamino)-2-pyridyl]p

1-[5-Aminoindolyl-2-carbonyl]-4-[3-(1-methylethylamino)-2-pyridyl]piperazine (EXAMPLE 7, 0.30 g, 0.79 mmol) is dissolved in 1.6 ml of methylene chloride and pyridine (0.064 ml, 0.79 mmol) is added. The reaction is cooled to 0° and methyl chloroformate (0.06 ml, 0.79 mmol) is added dropwise. The reaction is stirred for 2 hr at 0° and the reaction was stored at 0° for 18 hr. Then it was diluted with chloroform, washed with water, saline, dried over anhydrous sodium sulfate and concentrated under reduced pressure. Purification by recrystallization from methanol/hexane gives the title compound, mp 230°–231°.

Example 74

1-[5-(1',1'-dioxo-2'-isothiazolidinyl)indolyl-2-carbonyl]-4-[3-(1-methylethylamino)-2-pyridyl]piperazine 1-[5-(3-Chloropropylsulfonamidoindolyl-2-carbonyl]-4-[3-(1-methylethylamino)-2-pyridyl]piperazine (PREPARATION 86, 0.60 g, 1.16 mmol) is dissolved in 5.8 ml of acetonitrile and 0.115 ml of piperidine (3.48 mmol) and 0.174 g of sodium iodide (1.16 mmol) is added and the reaction was refluxed for 28 hr. Then the reaction is diluted with chloroform, washed with saturated sodium bicarbonate, water, dried over anhydrous magnesium sulfate and concentrated under reduced pressure. Purification by flash column chromatography eluting with methanol/chloroform (2.5/97.5), pooling and concentration of the appropriate fractions gives the title compound, mp 215°–217°.

Example 75

1-[5-(4-Methylpiperazin-1-ylcarbonylamino)indolyl-2-carbonyl]-4-[3-(1,1-dimethylethylamino)-2-pyridyl]piperazine (I)

Following the general procedure of EXAMPLE 6, and making non-critical variations but substituting 1-[3-(1,1-dimethylethylamino)-2-pyridyl]piperazine (PREPARATION 97) for 1-[3-(1-methylethylamino)-2-pyridinyl]piperazine and 5-(4-methylpiperazin-1-ylcarbonylamino)indole-2-carboxylic acid (PREPARATION 101) for 5-nitroindole-2-carboxylic acid, the title compound is obtained, mp 183°–185°.

Example 76

1-[5-(Trifluoromethanesulfonamido)indolyl-2-carbonyl]-4-[3-(1-methylethylamino)-2-pyridyl]piperazine 1-[5-aminoindole-2-carbonyl]-4-[3-(1-methylethylamino)-2-pyridyl]piperazine (EXAMPLE 7, 1.0 g) is dissolved in 18 ml of dichloromethane and cooled to −78°. Then triethylamine (0.37 ml) is added followed by the dropwise addition of triflic anhydride (0.45 ml) and the reaction is stirred for 1 hr. Then it is diluted with chloroform, extracted with saturated aqueous sodium bicarbonate, dried and concentrated. Purification by flash column chromatography eluting with ethyl acetate/hexane (60/40) and recrystallization from ethyl acetate/hexane gives the title compound, mp 282°–283°.

CHART A
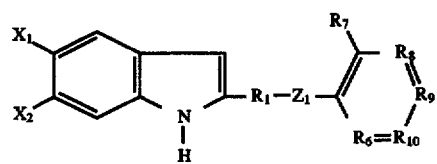
(I)
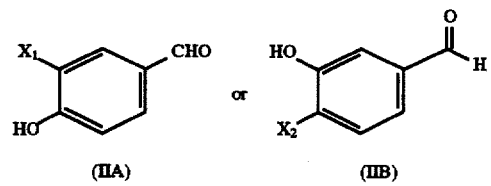
(IIA)    (IIB)
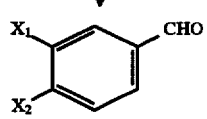
(III)
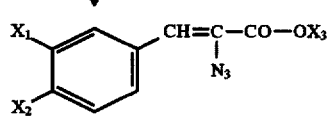
(IV)
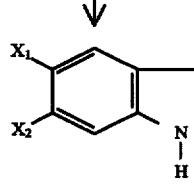
(V)
hydrolysis
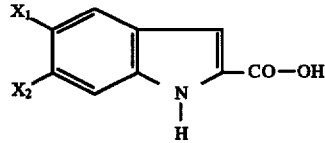
(IV)
Coupling
-continued
CHART A
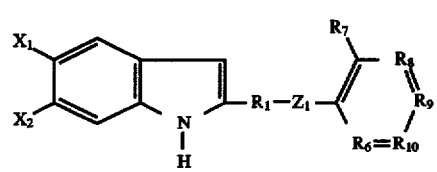
(I)
CHART B
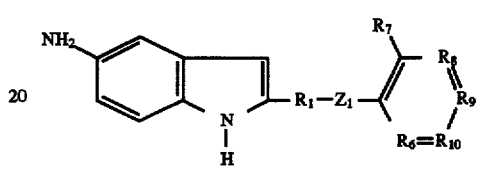
(VII)
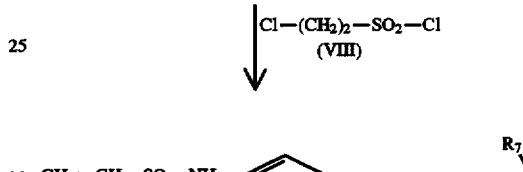
(VIII)
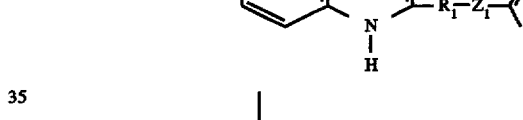
(IX)
(I)
I claim:
1. 1-[3-(1-Methylethylamino)-2-pyridinyl]piperazine.
* * * * *